United States Patent [19]
Todd et al.

[11] Patent Number: 5,210,228
[45] Date of Patent: May 11, 1993

[54] DECALINE BASED HMC-COA REDUCTASE INHIBITORS WITH TWO C-6 SUBSTITUENTS

[75] Inventors: Richard S. Todd, Burnham; Christopher N. Lewis, Cowley St. John; Alan H. Davidson; Alan H. Drummond, both of Witney, all of England

[73] Assignee: British Bio-Technology Limited, Oxford, England

[21] Appl. No.: 760,727

[22] Filed: Sep. 16, 1991

[30] Foreign Application Priority Data

Jan. 4, 1991 [GB] United Kingdom ............... 9100174

[51] Int. Cl.$^5$ ............... C07D 309/30; A61K 31/365
[52] U.S. Cl. ................... 549/292; 560/119
[58] Field of Search ............. 549/292; 560/119; 514/460, 510

[56] References Cited

U.S. PATENT DOCUMENTS

| | | | |
|---|---|---|---|
| 4,293,496 | 10/1981 | Willard | 562/501 |
| 4,444,784 | 4/1984 | Hoffman et al. | 549/292 |
| 4,661,483 | 4/1987 | Hoffman et al. | 514/236 |
| 4,668,699 | 5/1987 | Hoffman et al. | 514/460 |
| 4,771,071 | 9/1988 | Hoffman et al. | 514/460 |
| 4,866,090 | 9/1989 | Hoffman et al. | 549/264 |

FOREIGN PATENT DOCUMENTS 0142146 5/1985 European Pat. Off. .
0251625 1/1988 European Pat. Off. .

OTHER PUBLICATIONS

A. Endo, et al. Journal of Antibiotics 29: 1346–1348 (1976).
A. W. Alberts, et al., J. Proc. Natl. Acad. Sci. U.S.A. 77:3957 (1980).
Y. K. T. Lam et al., Journal of Antibiotics 34:614–616 (1981).
G. Albers-Schonberg et al., Journal of Antibiotics 34:507–512 (1981).
N. Serizawa et al., Journal of Antibiotics 36:604–607 (1983).
W. F. Hoffman et al., J. Med. Chem 29:849–852 (1986).
Kau-Ming Chen et al., Chemistry Letters, 1923–1926 (1987).
Rosen et al., Tetrahedron 42: 4909–4951 (1986).
Theisen et al., J. Org. Chem. 53: 2374–2378 (1988).

Primary Examiner—C. Warren Ivy
Assistant Examiner—Ba K. Trinh
Attorney, Agent, or Firm—Allegretti & Witcoff, Ltd.

[57] ABSTRACT

Compounds of either of general formulae I and II:

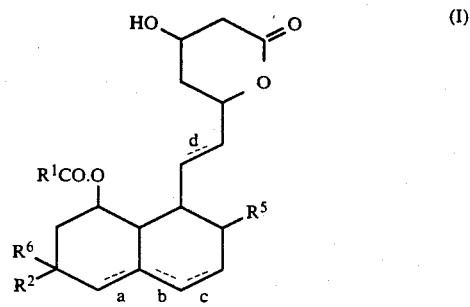

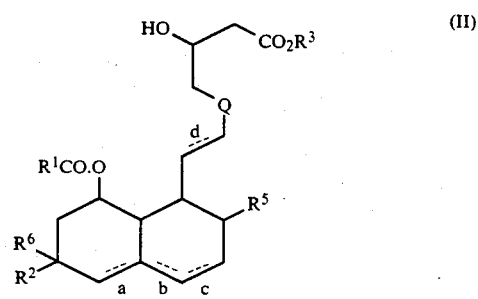

wherein:
$R^1$, $R^2$, $R^3$, $R^5$, $R^6$, a, b, c, and d are variables.

These compounds are useful in the treatment of hypercholesterolaemia in general and arteriosclerosis, familial hypercholesterolaemia or hyperlipidaemia in particular.

6 Claims, 9 Drawing Sheets

SCHEME 1

SCHEME VI

SCHEME IX

M = Lithium, sodium or similar
R = lower alkyl (pref Me)

DECALINE BASED HMC-COA REDUCTASE INHIBITORS WITH TWO C-6 SUBSTITUENTS

This invention relates to pharmaceutically active compounds, which are substituted decalins. The compounds of the present invention are inhibitors of the enzyme 3-hydroxy-3-methylglutaryl coenzyme A reductase (HMG-GoA reductase), the rate limiting enzyme in the biosynthesis of chloesterol in mammals including man, and as such are useful in the treatment of hypercholesterolaemia and hyperlipidaemia. Clinical evidence shows that reduction of serum cholesterol levels leads to a decreased risk of heart disease.

The natural fermentation products compactin (disclosed by A. Endo, et al. in *Journal of Antibiotics*, 29, 1346–1348 (1976)) and mevinolin (disclosed by A. W. Alberts, et al. in *J. Proc. Natl. Acad. Sci. U.S.A.*, 77, 3957 (1980)) are very active antihypercholesterolaemic agents which limit cholesterol biosynthesis by inhibiting the enzyme 3-hydroxy-3-methylglutaryl coenzyme A (HMG-CoA) reductase, the rate-limiting enzyme and natural point of cholesterolgenesis regulation in mammals, including man. Compactin (R=H, a=double bond) and mevinolin (R=—CH$_3$, a=double bond; also known as lovastatin) have the structures shown below:

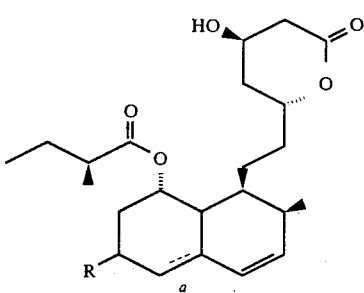

Also known in the art are the natural products dihydrocompactin (R=H, a=single bond) disclosed by Y. K. T. Lam et al., *Journal of Antibiotics*, 34, 614–616 (1981), dihydromevinolin (R=—CH$_3$, a=single bond) disclosed by G. Alberts-Schonberg et al., *Journal of Antibiotics*, 34, 507–512 (1981), and eptastatin (R=β-OH, a=double bond) disclosed by N. Serizawa et al., in *Journal of Antibiotics*, 36, 604–607 (1983).

U.S. Pat. No. 4,293,496 (Willard) discloses a number of semisynthetic analogues of mevinolin having the structure

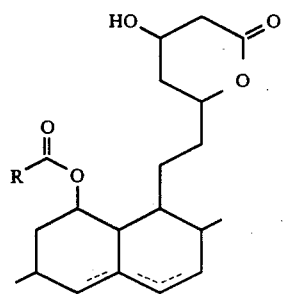

where the dotted lines represent single or double bonds and R is C$_{1-8}$ straight chain alkyl, C$_{3-10}$ branched chain alkyl except (S)-2-butyl, C$_{3-10}$ cycloalkyl, C$_{2-10}$ alkenyl, C$_{1-10}$ CF$_3$ substituted alkyl, halophenyl, phenyl C$_{1-3}$ alkyl and substituted phenyl C$_{1-3}$ alkyl.

U.S. Pat. No. 4,444,784, U.S. Pat. No. 4,661,483, U.S. Pat. No. 4,668,699 and U.S. Pat. No. 4,771,071 (Hoffman) disclose compounds of similar structure where the R group contains extra functional groups, for example ether, amide and ester groups.

In *J. Med. Chem.*, 29, 849–852 (1986), W. F. Hoffman et al. report the synthesis and testing of a number of the analogues referred to above, the preferred compound (now known as simvastatin) having the structure

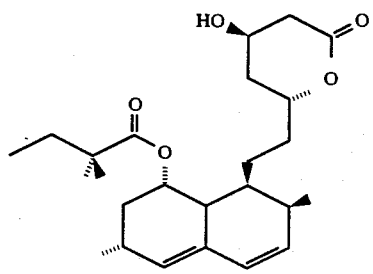

EP-A-0251625 (Inamine) discloses compounds of structure

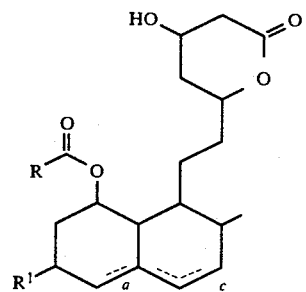

where R is similar to the corresponding group in the compounds described above, R$^1$ is a group of formula CH$_2$OH, CH$_2$OCO.R$^3$, CO$_2$R$^4$ or CO.NR$^6$R$^7$ wherein R$^3$, R$^4$, R$^6$, and R$^7$ can cover a range of alkyl, alkoxy, or aryl groups, and the dotted lines represent single or double bonds. Only one of these compounds, in which R$^1$ is CH$_2$OCO.NHPh, R is 1,1-dimethylpropyl and a and c are double bonds has a disclosed activity better than that of mevinolin. In general, the above patent publications also cover compounds in which the delta lactone has been hydrolysed to a delta hydroxy acid or a salt of that acid.

EP-A-0142146 discloses compounds of structure

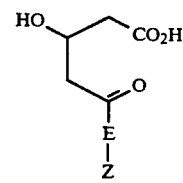

where E is —CH$_2$—CH$_2$—, —CH=CH— or —(CH$_2$)$_3$— and Z is (amongst others) a substituted decalin system of the same form as in those compounds referred to above.

EP-A-0323867 discloses the compound 6(R)-[2-[8(S)-(2,2-dimethylbutyryloxy)-2(S)-6,6-di-methyl-1,2,3,4,4a-

(S)5,6,7,8,8a(S)decahydronapthyl-1(S)]ethyl]-4-R-hydroxy-3,4,5,6-tetrahydro 2H pyran-2-one.

None of the cited patents and articles disclose or suggest the possibility of preparing the compounds of the present invention. The unique pattern of substituents on the decalin ring system differs from the cited art, whilst the compounds exhibit potent HMG-CoA activity.

The present invention provides novel decalin based compounds which are potent inhibitors of the enzyme 3-hydroxy-3-methylglutaryl coenzyme A (HMG-CoA) reductase and, therefore, are useful in the treatment or prevention of hypercholesterolaemia, hyperlipoproteinaemia and atherosclerosis.

According to a first aspect of the invention, there is provided a compound of either of general formulae I and II:

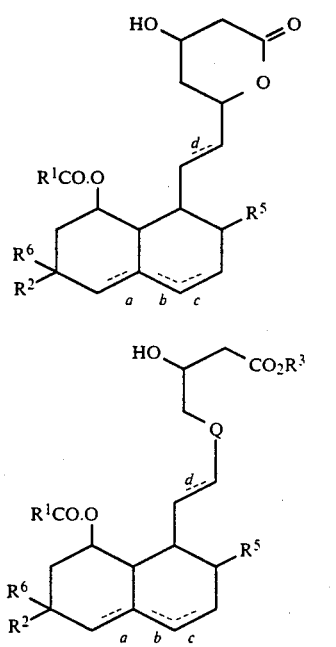

wherein:

$R^1$ represents a $C_{1-8}$ alkyl, $C_{3-8}$ cycloalkyl, $C_{3-8}$ cycloalkyl($C_{1-8}$)alkyl, $C_{2-8}$ alkenyl, or $C_{1-6}$ alkyl substituted phenyl group;

$R^2$ represents a $C_{1-8}$ alkyl, $C_{2-8}$ alkenyl, or a $C_{2-8}$ alkynyl group or a $C_{1-5}$ alkyl, $C_{2-5}$ alkenyl, or $C_{2-5}$ alkynyl group substituted with a substituted phenyl group;

$R^3$ represents a hydrogen atom or a substituent $R^4$ or M;

$R^4$ represents a $C_{1-5}$ alkyl group, or a $C_{1-5}$ alkyl group substituted with a group chosen from substituted phenyl, dimethylamino and acetylamino;

$R^5$ represents a hydrogen atom or a methyl or ethyl group, except that when both $R^2$ and $R^6$ represent a methyl group then $R^5$ is not methyl;

$R^6$ represents a $C_{1-8}$ alkyl, $C_{2-8}$ alkenyl or a $C_{2-8}$ alkynyl group or a $C_{1-5}$ alkyl, $C_{2-5}$ alkenyl or $C_{2-5}$ alkynyl group substituted with a substituted phenyl group;

M represents a cation capable of forming a pharmaceutically acceptable salt;

Q represents C=O or CHOH; and each of a, b, c, and d is independently a single or double bond except that when a and c are double bonds then b is a single bond.

The term "$C_{1-8}$ alkyl" refers to a straight or branched chain alkyl moiety having one to eight carbon atoms, including for example, methyl, ethyl, propyl, isopropyl, butyl, sec-butyl, pentyl, dimethyl-propyl, hexyl, and octyl, and cognate terms (such as "$C_{1-8}$ alkoxy") are to be construed accordingly. Similarly, the term "$C_{1-5}$ alkyl" refers to a straight or branched chain alkyl moiety having one to five carbon atoms (such as methyl or ethyl).

The term "$C_{3-8}$ cycloalkyl" refers to a saturated alicyclic moiety having from 3 to 8 carbon atoms arranged in a ring and includes, for example, cyclopropyl, cyclobutyl, cyclopentyl, and cyclooctyl.

The term "$C_{2-8}$ alkenyl" refers to a straight or branched chain alkyl moiety having one to eight carbon atoms and having in addition at least one double bond, of either E or Z stereochemistry where applicable. This term would include, for example, vinyl, 1-propenyl, 1-and 2-butenyl and 2-methyl-2-propenyl.

The term "$C_{2-8}$ alkynyl" refers to a straight or branched chain alkyl moiety having one to eight carbon atoms and having in addition at least one triple bond. This term would include, for example, propargyl, and 1-and 2-butynyl.

The term "substituted", as applied to a phenyl or other aromatic ring, means substituted with up to four substituents each of which independently may be $C_{1-6}$ alkyl, $C_{1-6}$ alkoxy, hydroxy, thiol, amino, halo (including fluoro, chloro, bromo, and iodo), trifluoromethyl or nitro.

The phrase "a pharmaceutically acceptable salt" as used herein and in the claims is intended to include non-toxic alkali metal salts such as sodium, potassium, calcium and magnesium, the ammonium salt and salts with non-toxic amines such as trialkylamines, dibenzylamine, pyridine, N-methylmorpholine, N-methylpiperidine and other amines which have been or can be used to form salts of carboxylic acids.

There are several chiral centres in the compounds according to the invention because of the presence of asymmetric carbon atoms. The presence of several asymmetric carbon atoms gives rise to a number of diastereoisomers with the appropriate R or S designated stereochemistry at each asymmetric centre. General Formulae I and II and, where appropriate, all other formulae in this specification are to be understood to include all such stereoisomers and mixtures (for example racemic mixtures) thereof.

Disregarding any asymmetric centres that may be present in the groups $R^1$, $R^2$, $R^3$, $R^4$ and $R^6$, the preferred relative and absolute stereochemistry is as shown in formulae IIIA and IIIB, mutatis mutandis. More specifically for the compounds IIIA and IIIB the Cahn, Ingold, Prelog designations for the absolute configurations are 4'(R), 6'(R), 1(S), 2(S), 4a(R), 8(S), 8a(S).

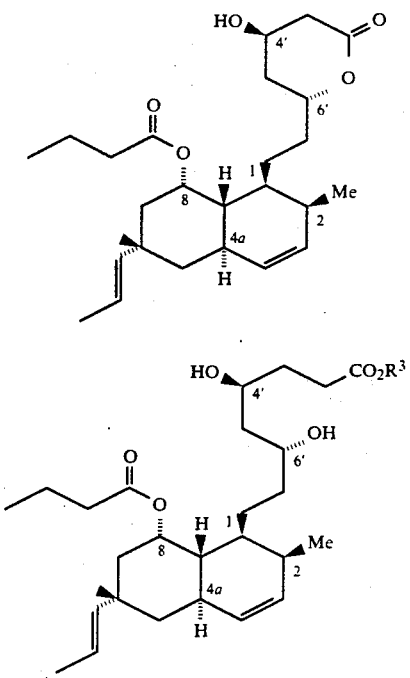

It is preferred that all of the compounds of general formulae I and II should have (wherever possible) the same spacial orientation of groups at each chiral carbon atom and therefore belong to the same stereochemical series. The R-S designation for each centre may not be identical to that found for compound IIIA and IIIB because of the details of the sequence rules for determining that designation. Clearly in compounds in which a or b are double bonds then the carbon atom labelled C-4a will not be an asymmetric centre, and in compounds of Formula II in which Q is the group C=O then the carbon atom labelled C-6' is not an asymmetric centre.

Compounds of the formula IIIB are preferred.

In compounds of Formula II in which Q is the group CHOH, the preferred stereochemistry is that in which the two carbon atoms bearing the hydroxy groups have the same spacial arrangement as the corresponding carbon atoms in the lactone in compound IIIA. The preferred isomer is referrred to as the syn diol.

Each M is preferably free from centres of asymmetry and is more preferably sodium, potassium or ammonium, and most preferably sodium. For simplicity, each formula in which an M appears has been written as if M were monovalent and, preferably, it is. However, M may also be divalent or trivalent and, when it is, it balances the charge of two or three carboxylic acid groups, respectively. Thus Formula II and every other formula containing an M embraces compounds wherein M is divalent or trivalent, e.g. compounds containing two or three mono carboxylate-containing anions per cation M.

Preferred compounds include those in which independently or in any combination:

$R^1$ represents $C_{4-6}$ branched alkyl;
$R^2$ represents $C_{2-6}$ alkenyl or $C_{2-5}$ alkenyl optionally substituted with substituted phenyl;
$R^3$ is $R^4$;
$R^4$ represents $C_{1-5}$ alkyl (and more preferably methyl or ethyl) or M;
$R^6$ represents $C_{1-5}$ alkyl;
Q represents CHOH; and/or
b and d are both single bonds, and one or both of a and c are double bonds.

A preferred subgroup of compounds of either general formula I or of general formula II are those wherein $R^1$ represents a $C_{4-6}$ branched alkyl group; $R^2$ represents a $C_{2-6}$ alkenyl group; each of a and c independently represents a single or double bond; and each of b and d represents a single bond. Alternatively or in addition $R^6$ represents a $C_{1-5}$ alkyl group (e.g. methyl).

Particularly preferred compounds of this subgroup are those wherein $R^1$ represents a $C_{4-5}$ branched alkyl group; $R^2$ represents (E)-prop-1-enyl; and $R^5$ represents methyl. Illustrative compounds are:

(A) (1S,2S,4aR,6S,8S,8aS,4'R,6'R)-6'-{2-(1,2,4a,5,6,7,8,8a-octahydro-2,6-dimethyl-8-[(2'',2''-dimethyl-1''-oxobutyl)oxy]-6-[(E)-prop-1-enyl]-1-naphthalenyl)ethyl}-tetra-hydro4'-hydroxy-2H-pyran-2'-one (B) Sodium (1S,2S,4aR,6S,8S,8aS,3'R,5'R)-7'-(1,2,4a,5,6,7,8,8a-octahydro-2,6-dimethyl-8-[(2'',2''-dimethyl-1'-oxobutyl)oxy]-6-[(E)-prop-1-enyl]-1-naphthalenyl)-3', 5'-dihydroxyheptanoate (C) Methyl (1S,2S,4aR,6S,8S,8aS,3'R,5'R)-7'-(1,2,4a,5,6,7,8,8a-octahydro-2,6-dimethyl-8-[(2'',2''-dimethyl-1''-oxobutyl)oxy]-6-[(E)-prop-1-enyl]-1-naphthalenyl)-3',5'-dihydroxyheptanoate (D) Methyl (1S,2S,4aR,6S,8S,8aS,3'R)-7'-(1,2,4a,5,6,7,8,8a-octahydro-2,6-dimethyl-8-[(2'',2''-dimethyl-1''-oxobutyl)oxy]-6-[(E)-prop-1-enyl]-1-naphthalenyl)-3'-hydroxy-5'-oxoheptanoate For simplicity the compounds of Formula II may be subdivided according to the exact form of $R^3$ and Q. Thus the compounds in which Q is the group C=O and $R^3$ is M or hydrogen (which may be represented by Y) are considered to be compounds of the subgroup IIe, whereas if $R^3$ is a group of formula $R^4$ the ketones are in the subgroup IIa. Compounds in which Q is the group CHOH and $R^3$ is a group of form $R^4$ make up the subgroup IIb, when $R^3$ is hydrogen the compounds are of subgroup IIc, and when $R^3$ is a group of formula M the compounds are of the subgroup IId.

The present invention also provides novel processes for the preparation of compounds of general formulae I and II as well as certain intermediates in their preparation, as will now be described by reference to the drawings, in which.

Figure 1:
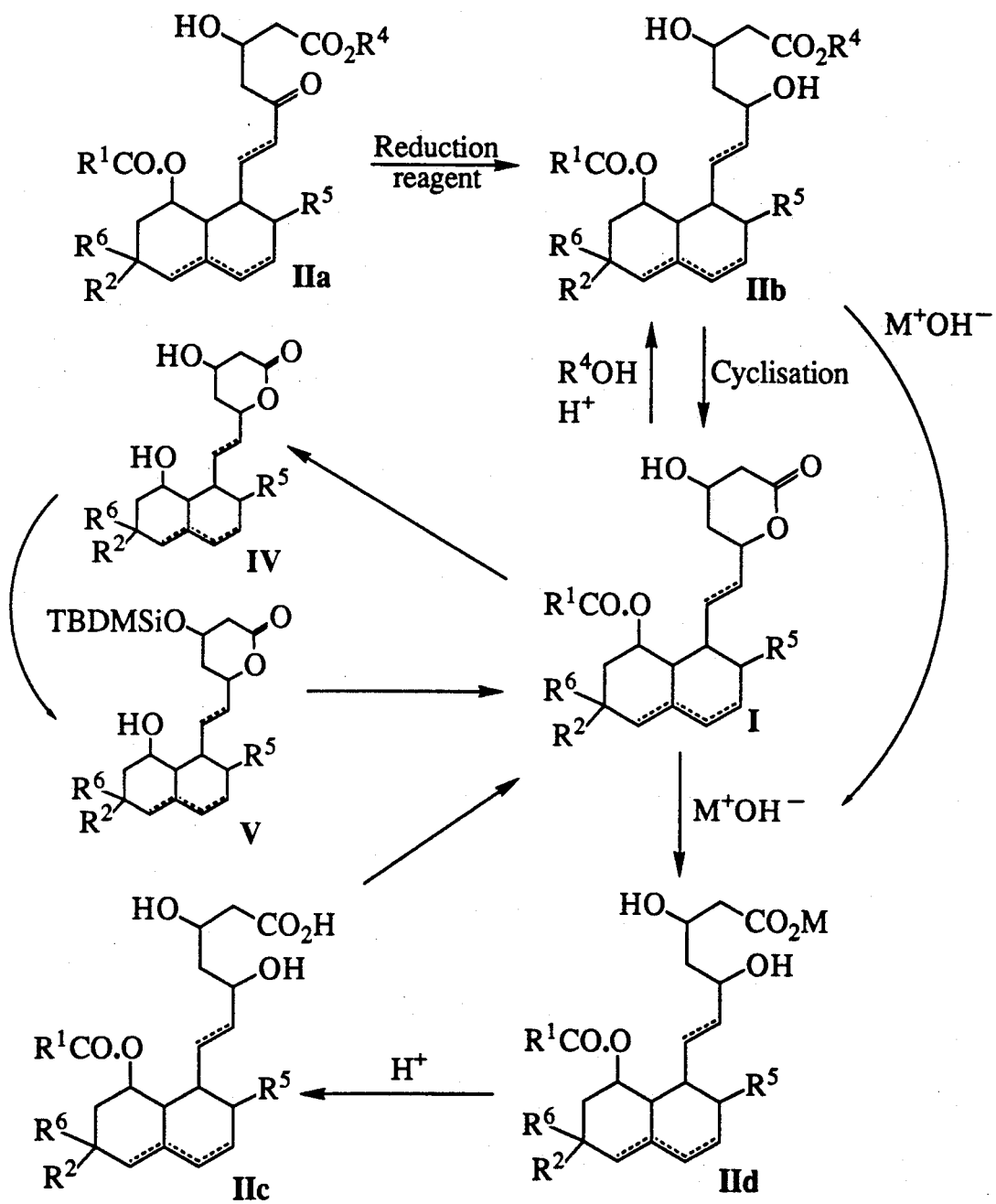
FIG. 1 shows reaction scheme I, which shows the interconversion of compounds of general formula I with subgroups IIa, IIb, IIc and IId and the interconversion of compounds of general formula I with compounds of general formulae IV and V.
Figure 2:
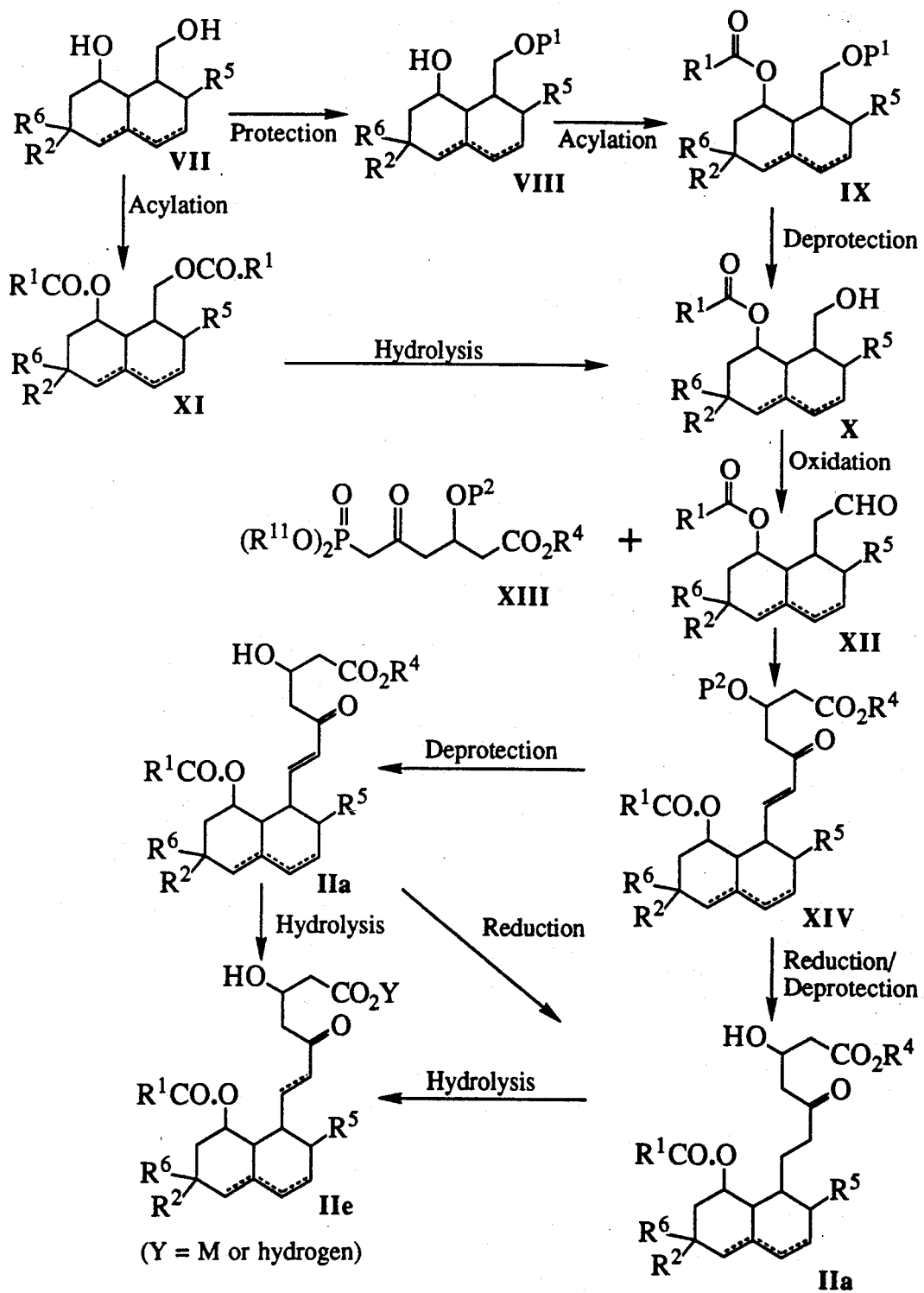
FIG. 2 shows reaction scheme II, which shows a preparative route of compounds of subgroups IIa and IIe from compounds of general formula XIV, which in turn are preparable from compounds of general formula VII.
Figure 3:
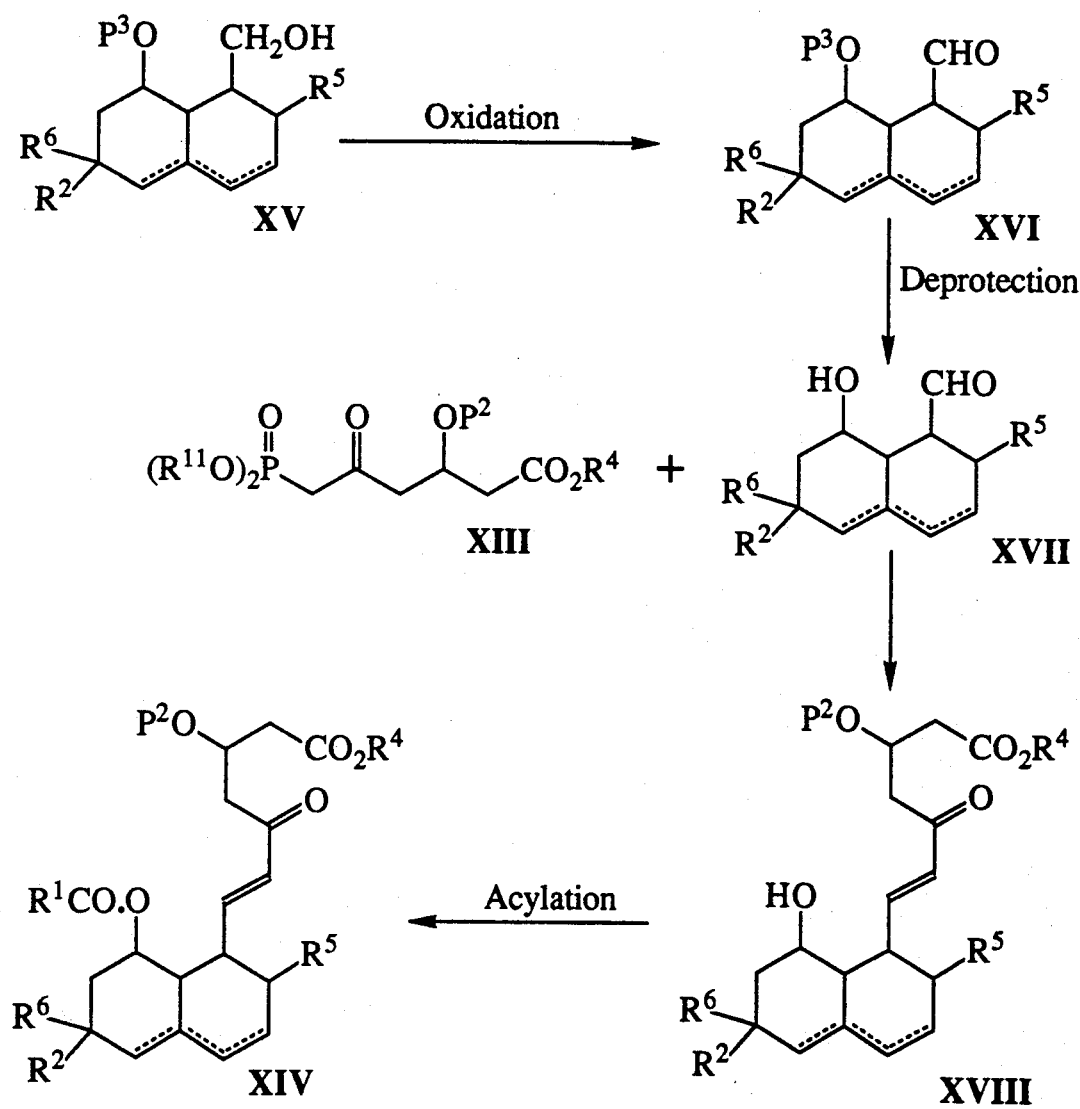
FIG. 3 shows reaction scheme III, which shows a different preparative route of compounds of general formula XIV, this time from compounds of general formula XV.
Figure 4:
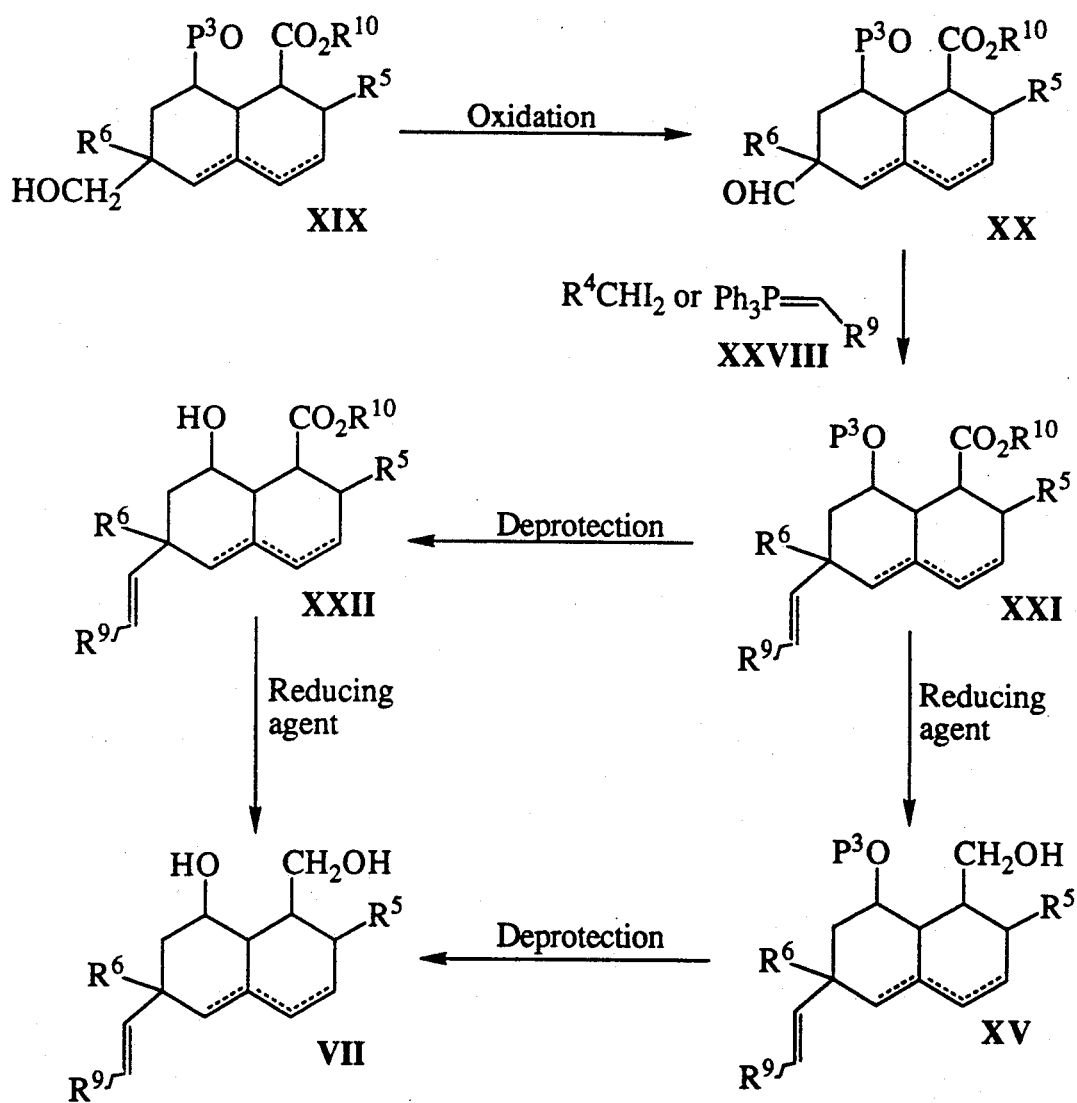
FIG. 4 shows reaction scheme IV, which shows a preparative route of compounds of general formulae VII and XV from compounds of general formulae XXI and/or XXII, which in turn may be prepared from compounds of general formula XIX.
Figure 5:
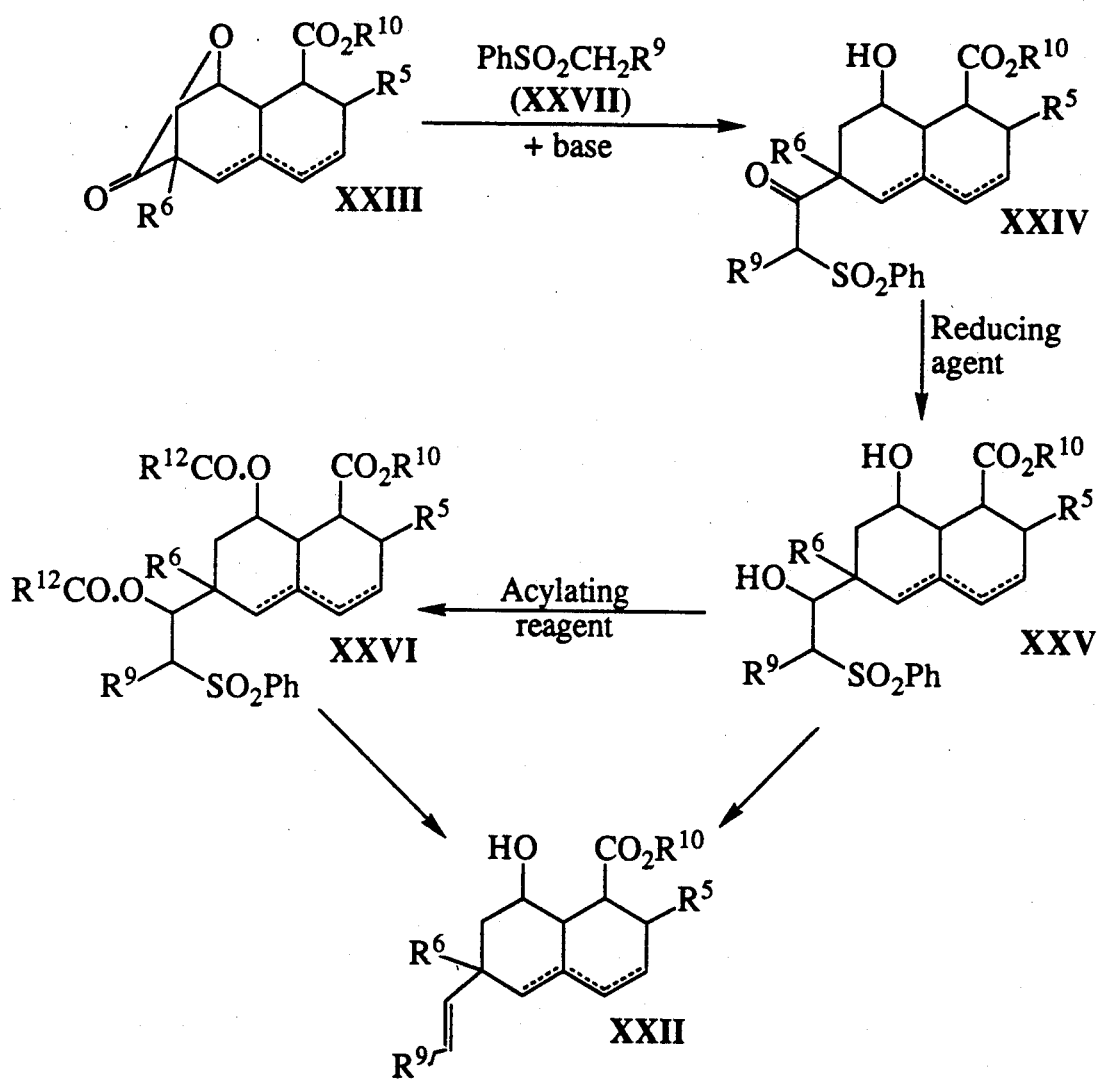
FIG. 5 shows reaction scheme V, which shows a further preparative route for compounds of general formula XXII.
Figure 6:
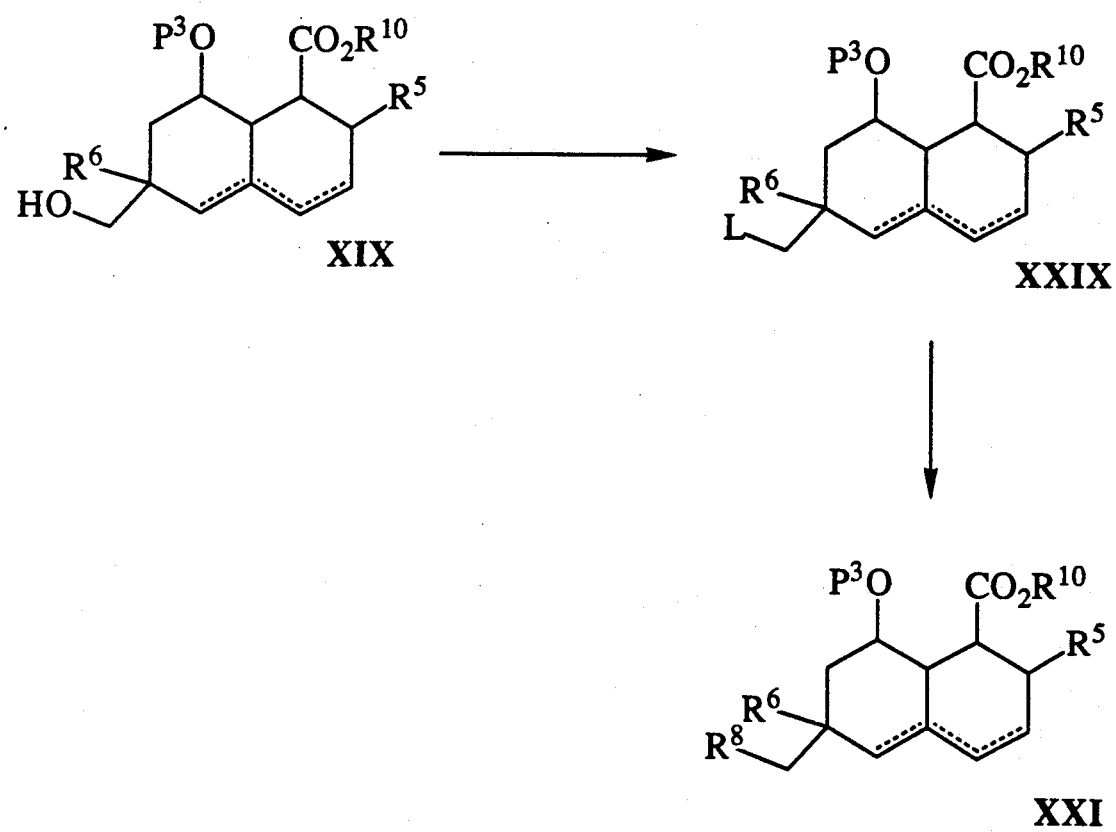
FIG. 6 shows reaction scheme VI, which shows a further preparative route for compounds of general formula XXI.
Figure 7:
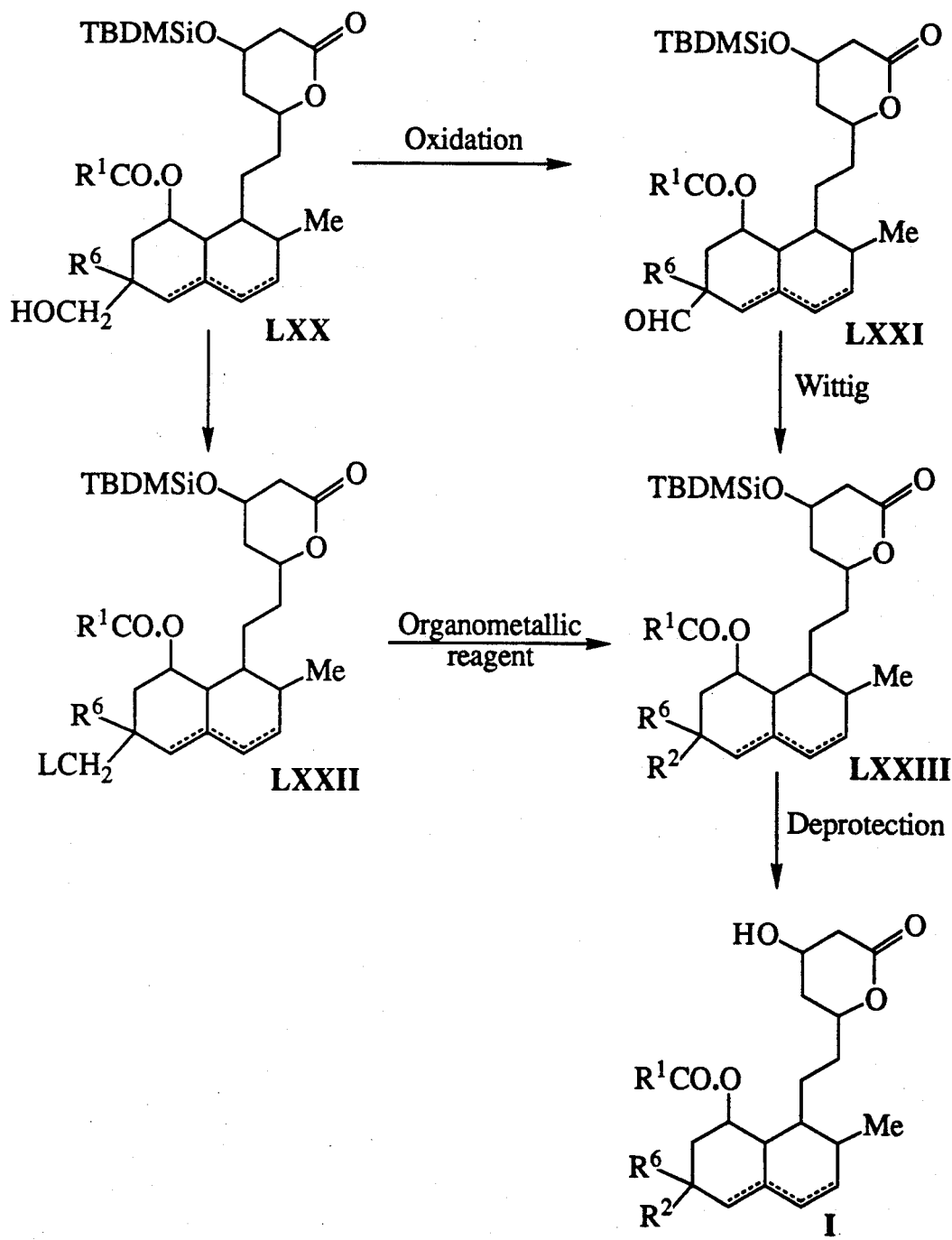
FIG. 7 shows reaction scheme VII, which shows a further route for the preparation of compounds of general formula I.
Figure 8:
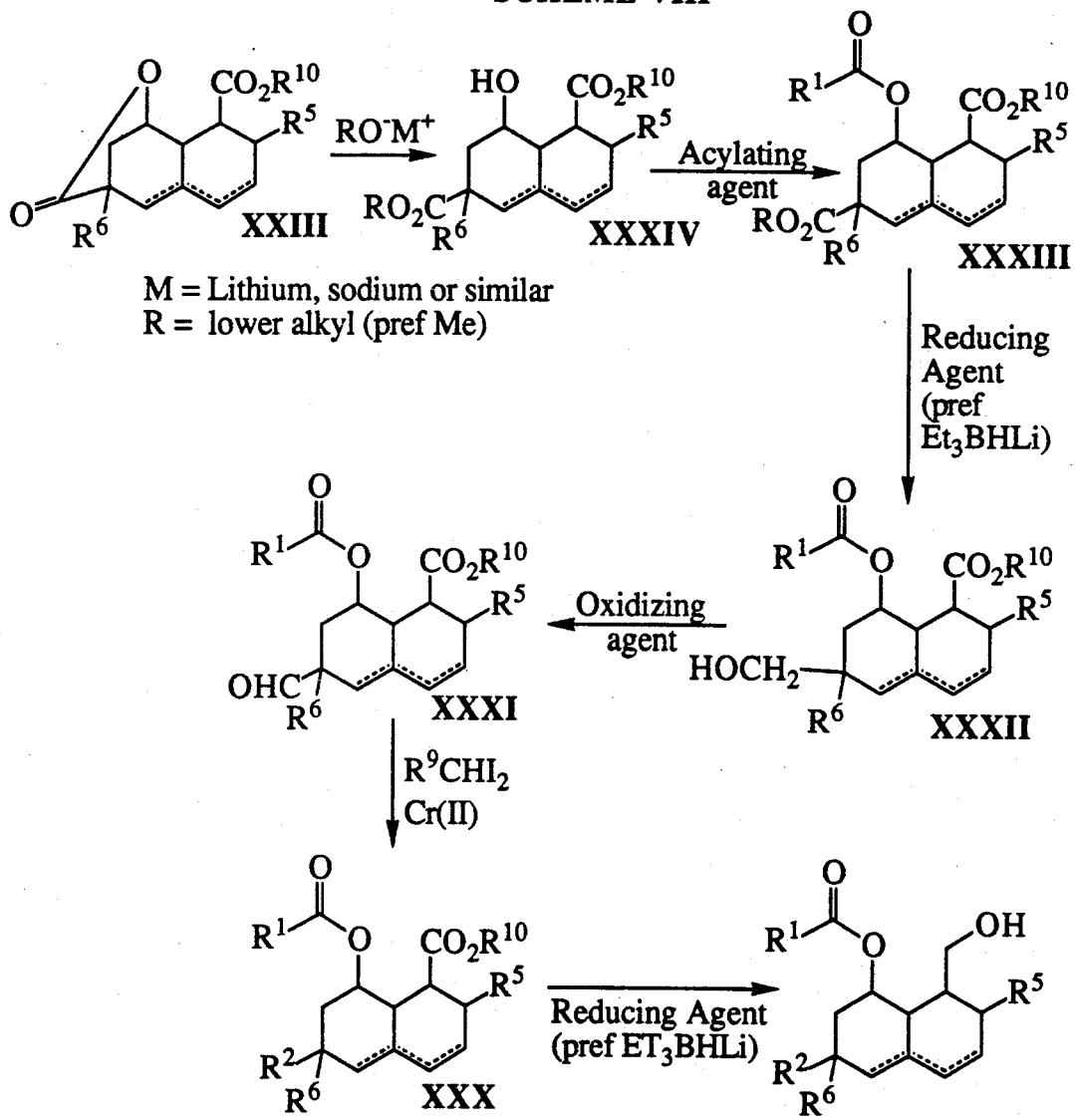
Figure 9:
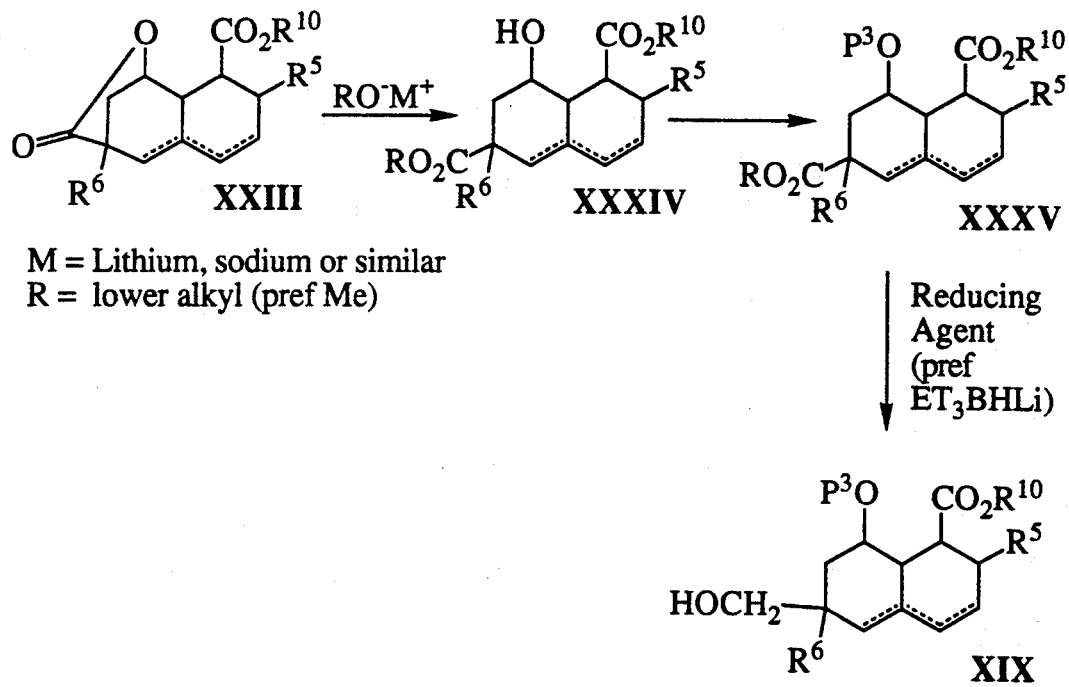

FIG. 8 shows reaction scheme VIII, which shows a different preparative route of compounds of formula X; and FIG. 9 shows reaction scheme IX, which shows a further preparative route for compounds of the general formula XIX The compounds of the various subgroups IIa–IId of general formula II (hereafter referred to as general formulae IIa to IId), and those of general formula I, may be prepared by the general reaction route shown in Scheme I in which $R^1$, $R^2$, $R^4$, $R^5$, $R^6$ and M are as previously defined. Unless the context otherwise requires, substituents in the general formulae in Schemes I and II have the same values as the corresponding substituents in general formulae I and II.

According to a second aspect of the invention, there is provided a process for the preparation of a compound of either of general formulae I and II, the process comprising:

(a) deprotecting and optionally reducing a compound of general formula XIV as shown in Scheme II to form a compound of general formula IIa; or (b) when $R^5$ represents methyl, deprotecting a compound of general formula LXXIII to form a compound of general formula I; and (c) optionally after step (a) or (b) converting a compound of general formula I or IIa directly or indirectly into another compound of general formula I or II.

A ketone of general formula IIa may be reduced to a dihydroxy ester of general formula IIb by reduction of the ketone group with a reducing agent, such as those well known in the art, e.g. sodium borohydride, sodium cyanoborohydride, zinc borohydride, lithium tri-s-butylborohydride or other similar reducing agents that will not reduce the ester functionality. Preferably, the reaction is carried out in such a manner as to maximize the production of the preferred syn isomer of the compound of general formula IIb. The stereoselective reduction of compounds of general formula IIa is preferably carried out in two stages, in the first stage the ketone ester is reacted with a trialkylborane, preferably tri-n-butyl borane, or an alkoxydialkylborane, preferably methoxydiethylborane or ethoxydiethylborane (*Chemistry Letters*, 1987, 1923-1926) at ambient temperature in an inert organic solvent such as tetrahydrofuran, diethyl ether, or 1,2-dimethoxyethane, and optionally in the presence of a protic solvent such as methanol or ethanol, and preferably in a mixture of tetrahydrofuran and methanol. The complex which is thus produced is then reduced with sodium borohydride at a temperature between −78° C. and −20° C. The resulting compound of general formula IIb produced from the stereoselective reduction contains two asymmetric carbon atoms bearing hydroxyl groups in a syn configuration. Thus reduction of the ketone radical under the conditions described herein produces mostly the syn isomers of compounds of general formula IIb and only a small amount of the less preferred anti isomers.

The ratio of isomers produced will vary according to the specific compound utilized and the reaction conditions employed. Normally, this ratio will be approximately 9:1 to 9.8:0.2. However, the use of a non-specific reduction method will normally produce a near 1:1 mixture of diastereoisomers. Nevertheless, the mixture of isomers may be separated and purified by conventional techniques and then converted to the compounds of general formula I in a conventional manner well-known to those skilled in the art.

Compounds of general formula IIb may be cyclised to the corresponding lactones of general formula I for example by heating in an inert organic solvent such as benzene, toluene or xylene and azetropically removing the alcohol which is produced. Preferably, the lactonisation is carried out by heating the compound of general formula IIb with an acid, preferably p-toluenesulphonic acid, in benzene or toluene, evaporating the solvent and alcohol thus formed, and repeating the process until all of the compound of general formula IIb has been consumed. If the relative stereochemical configuration of the two carbon atoms bearing the hydroxy groups are established as syn in general formula IIb, then lactonisation will produce the preferred trans lactone of general formula I, otherwise the lactonization will produce a mixture of trans and cis lactones.

A compound of general formula IId may be prepared from a compound of general formula IIb or a compound of general formula I by hydrolysis, preferably hydrolysis with a base such as lithium hydroxide, sodium hydroxide or potassium hydroxide in a mixture of water and an organic solvent such as methanol, ethanol or tetrahydrofuran at a temperature between 0° C. and 50° C. inclusive, preferably at ambient temperature. The cation in compounds of general formula IId is usually determined by the cation of the hydroxide employed; however, the cation may then be exchanged for another cation for example by treatment with ion-exchange resin.

Compounds of general formula IIc may be obtained from compounds of general formula IId by neutralisation, for example careful neutralisation with a mineral acid such as hydrochloric, sulphuric or nitric in aqueous solution, followed by extraction with an appropriate organic solvent. Alternatively, the acids of general formula IIc may be obtained by treating compounds of general formula IId with an ion exchange resin. If the acids of general formula IIc are allowed to stand in solution they slowly re-lactonise to the compounds of general formula I. This process may be accelerated by heating a solution of the acid under conditions that remove the water formed, such as in a Dean-Stark apparatus, or by stirring the solution with a drying agent such as anhydrous sodium sulphate, magnesium sulphate or molecular sieves.

Lactones of general formula I may, if desired, be hydrolysed in the presence of an alcohol and a catalytic amount of acid, preferably p-toluenesulphonic acid, to produce compounds of general formula IIb.

Compounds of general formulae I, IIb, IIc and IId may be converted to compounds of general formula I in which the ester group containing $R^1$ has been exchanged for another ester group, for example via a de-acylated intermediate using the methodology of U.S. Pat. No. 4,444,784. Thus a compound of general formula I, IIb, IIc or IId may be treated for extended periods, for example 1-3 days, with an alkaline metal hydroxide such as lithium hydroxide, sodium hydroxide or potassium hydroxide in a solvent such as water or an alcohol, and preferably a mixture of water and ethanol, until the ester group containing the group $R^1$ is removed. Mild acid treatment then closes the lactone ring to give an alcohol of general formula IV. The secondary alcohol of general formula IV is then selectively protected with a t-butyldimethylsilyl group under standard conditions to give an intermediate alcohol of general formula V, as shown in Scheme I. Acylation, for example using an acid halide or anhydride in the presence of a mild base such as triethylamine or pyridine, or by using an acid and an activating agent such as a carbodiimide and optionally using N,N-dimethylaminopyridine as a catalyst, in an inert solvent such as chloroform, followed by deprotection of the secondary hydroxyl group using tetrabutylammonium fluoride in tetrahydrofuran, buffered with acetic acid, gives a compound of general formula I in which the original group $R^1$ has been exchanged for a different group of formula $R^1$.

A ketone of general formula IIa may be prepared by the methods outlined in Scheme II, in which $R^1$, $R^2$, $R^4$, and $R^5$ and $R^6$ are as previously described, and $P^1$, $P^2$ and $R^{11}$ are defined below.

Compounds of Formula IIa wherein d is a double bond may be prepared by removing the protecting group $P^2$ from compounds of formula XIV. This may be achieved in the preferred cases in which $P^2$ is trialkylsilyl or alkyldiarylsilyl by the use of conditions that generate fluoride anions, and preferably by using tetrabutyl-ammonium fluoride in tetrahydrofuran buffered with acetic acid or hydrofluoric acid in aqueous acetonitrile.

Compounds of Formula IIa wherein d is a single bond may be obtained from compounds of Formula IIa wherein d is a double bond by reduction of the carbon-carbon double bond of the enone system, using reagents and conditions that do not affect the other functional groups present.

Examples of such reagents are sodium hydrogen telluride, triphenyltin hydride, or tri-n-butyltin hydride with a palladium or platinum catalyst.

Compounds of Formula IIa wherein d is a single bond may also be prepared from enones of general formula XIV by reduction of the double bond followed by deprotection. For example it is possible to reduce the double bond in one reaction by treatment with such mixtures as tri-n-butyltin hydride with a palladium or platinum catalyst, or with a trialkylsilane, preferably triethylsilane, and a catalyst such as tris(triphenylphosphine)rhodium chloride [Wilkinson's catalyst] either neat, using an excess of the silane, or in an inert hydrocarbon solvent such as benzene or toluene at a temperature between ambient and reflux, preferably 50°–70° C. The crude silyl enol ether thus produced is treated with hydrofluoric acid in aqueous acetonitrile to give the compound general formula IIa in which d is a single bond.

However, the preferred method of transformation of compounds of general formula XIV is to treat the enone with a reducing agent, preferably sodium hydrogen telluride in an alcoholic solvent such as methanol or ethanol, and optionally in the presence of a mild buffer such as ammonium chloride, until the starting material is consumed. The protected alcohol thus produced may be purified in the usual way, or used crude, and then the compound may be treated with hydrofluoric acid in aqueous acetonitrile to give the compound general formula IIa in which d is a single bond.

Compounds of general formula IIe may be prepared from compounds of general formula IIa by hydrolysis with a base such as lithium hydroxide, sodium hydroxide or potassium hydroxide in a mixture of water and an organic solvent such as methanol, ethanol or tetrahydrofuran at a temperature between 0° C. and 50° C., preferably ambient temperature. The cation in compounds of general formula IIe is usually determined by the cation of the hydroxide employed; however, the cation may then be exchanged for another cation by treatment with, for example, ion-exchange resins. Compounds where $R^3$ is a hydrogen atom can be made by neutralisation of the solvent mixture and/or of the cationic compounds.

Compounds of general formula IIa may be used as intermediates in the production of compounds of general formulae IIb–e and of general formula I as detailed in Scheme I, or they may be used as HMG-CoA reductase inhibitors in their own right.

In compounds of general formulae I and II, the group $R^2$ may be modified to produce different compounds within the general formulae. Among the modifications that can be made are included reducing alkynes to alkenes, reducing alkenes to alkanes, isomerising between E and Z alkenes and/or moving double and/or triple bonds once within the chain.

An enone of general formula XIV may be prepared from an aldehyde of general formula XII by reaction with a phosphonate of general formula XIII in which $R^{11}$ is a lower (e.g. $C_{1-8}$ or, preferably, $C_{1-4}$) alkyl group such as methyl or ethyl, and the group $P^2$ is any group suitable for the protection of hydroxyl groups, but preferably trialkylsilyl or alkyldiarylsilyl. The reaction between the aldehyde of general formula XII and the phosphonate of general formula XIII may if convenient be carried out in either of the following two ways. In a first method the aldehyde of general formula XII and phosphonate of general formula XIII are reacted together in the presence of a chelating metal halide such as lithium chloride or magnesium bromide and a mild organic base such as triethylamine or 1,8-diazabicyclo[4.5.0]undec-7-ene (DBU) in an inert solvent such as acetonitrile or dimethylsulphoxide at ambient temperature. In a second method the phosphonate XIII is first treated with a strong organic base such as lithium diisopropylamide or lithium or sodium bis(trimethylsilyl)amide in an inert organic solvent such as diethyl ether or tetrahydrofuran at a temperature between −78° C. and 0° C., the aldehyde of general formula XII added at the same temperature, and the mixture allowed to warm to ambient temperature, all under an inert atmosphere.

An aldehyde of general formula XII may be prepared from an alcohol of general formula X by oxidation, for example by conventional oxidation reagents such as pyridinium chlorochromate or pyridinium dichromate, or by using a catalytic quantity of tetra-n-propylammonium per-ruthenate and N-methylmorpholine N-oxide, in an inert organic solvent such as dichloromethane or tetrahydrofuran, but preferably the oxidation is carried out using Swern's protocol. An intermediate alcohol of general formula X may be prepared for example in either of two ways from a diol of general formula VII. In the first method the diol of general formula VII is acylated for example by treatment with an excess of an acid anhydride (($R^1CO)_2O$) or acid halide ($R^1CO.Hal$) in the presence of a catalyst such as N,N-dimethylaminopyridine, and a base such as triethylamine or pyridine until both hydroxyl groups in the compound of general formula VII have reacted. The diacylated compound of general formula XI is then hydrolysed for example by treatment with an alkali metal hydroxide such as lithium hydroxide, potassium hydroxide or sodium hydroxide in a solvent such as water or an alcohol, or a mixture of such solvents, at a temperature between 0° C. and ambient for a time suitable to maximise the production of the alcohol X.

In the second and preferred of the two exemplary methods, the diol of general formula VII is treated under conditions that will selectively protect the primary alcohol, for example either as an ester or an ether. Such conditions are well known to one skilled in the art, but the preferred conditions are to treat with one equivalent of a trialkylsilylchloride or alkyldiarylsilylchloride in the presence of imidazole and, optionally, a mild organic base such as triethylamine or pyridine, and preferably using dichloromethane or chloroform as a solvent. The product of such a reaction will be a compound of general formula VIII wherein $P^1$ is a trialkylsilyl or alkyldiarylsilyl moiety or other protective group. The compound of general formula VIII is then acylated, for example using the conditions described above, that is treatment with the appropriate acid halide ($R^1CO.Hal$) or preferably the anhydride (($R^1CO)_2O$) using a mild organic base such as triethylamine or pyridine and optionally using a catalyst such as N,N-dimethylaminopyridine. The resulting intermediate, a compound of general formula IX, may then be deprotected to give an alcohol of general formula X using such conditions as are appropriate for the removal of the group $P^1$, without affecting the rest of the molecule. For the removal of the preferred trialkylsilyl or alkyldiarylsilyl groups, the preferred methods are to use tetrabutylammonium fluoride in an inert solvent such as tetrahydrofuran, or hydrofluoric acid in aqueous acetonitrile at ambient temperature. However, it will be appreciated by one skilled in the art that other methods are available for the removal of these preferred groups, or that other protecting groups may be used in the transformation of a diol of general formula VII to an alcohol of general formula X.

Intermediate compounds of general formula XIV may also be synthesised from the protected alcohols of general formula XV using the sequence of reactions shown in Scheme III, in which $R^2$, $R^4$, $R^5$, $R^{11}$ and $P^2$ are as previously defined, and $P^3$ is defined below.

An intermediate of general formula XIV may be prepared from an enone of general formula XVIII by acylation, for example using conventional means. Thus, a compound of general formula XIV may be prepared by treating an alcohol of general formula XVIII with an acid chloride or bromide ($R^1CO.Hal$), or preferably an anhydride (($R^1CO)_2O$) in the presence of a mild organic base such as pyridine or triethylamine, and preferably using a catalyst such as N,N-dimethylaminopyridine, either neat or in an inert solvent, preferably dichloromethane or chloroform at a temperature between 0° C. and reflux. Alternatively the transformation may be carried out using the acid ($R^1CO_2H$) and a coupling reagent such as a carbodiimide and a catalyst such as N,N-dimethylaminopyridine, in an inert solvent and preferably at ambient temperature.

An enone of general formula XVIII may be prepared from an aldehyde of general formula XVII and a phosphonate of general formula XIII as defined above for example by using a chelating metal halide such as lithium chloride or magnesium bromide and a mild organic base such as triethylamine or DBU in an inert organic solvent, preferably acetontrile or dimethylsulphoxide, at a temperature from 0° C. to ambient and preferably under an inert atmosphere.

To prepare an aldehyde of general formula XVII, an alcohol of general formula XV, in which the group $P^3$ is any group suitable for the protection of alcohols, (preferably trialkylsilyl or alkyldiarylsilyl) may be oxidised to an aldehyde of general formula XVI for example by conventional means such as pyridinium chlorochromate or pyridinium dichromate, or by using a catalytic quantity of tetra-n-propylammonium per-ruthenate (TPAP) in the presence of N-methylmorpholine N-oxide in an inert solvent, preferably dichloromethane, but most preferably by using Swern's protocol. The protecting group $P^3$ may then be removed by any appropriate method (but in the preferred case where $P^3$ is trialkylsilyl or alkyldiarylsilyl, the group may be removed by any method that generates fluoride ions, and preferably using hydrofluoric acid in aqueous acetonitrile, at ambient temperature under an inert atmosphere) to give a hydroxy aldehyde of general formula XVII.

Intermediate alcohols of general formulae VII and XV useful in the syntheses outlined in Schemes II and III may be prepared as shown in Scheme IV, in which $R^2$, $R^5$ and $P^3$ are as previously defined, $R^{10}$ is lower (e.g. $C_{1-8}$) alkyl, and $R^9$ is as defined below.

An intermediate alcohol of general formula XV may be prepared by reduction of the ester group in a compound of general formula XXI, for example using conventional reagents such as lithium aluminium hydride, diisobutylaluminium hydride or lithium triethylborohydride in an inert organic solvent such as diethyl ether or tetrahydrofuran, at ambient temperature to reflux, under an inert atmosphere. The alcohol of general formula XV may then be used as outlined in Scheme III or may be deprotected to give an alcohol of general formula VII, which may then be used as in Scheme II. The deprotection may be carried out by any means suitable for removal of the group $P^3$, but in the preferred cases in which the group $P^3$ is a trialkylsilyl or alkyldiarylsilyl group, the reaction is preferably carried out using hydrofluoric acid in aqueous acetonitrile, at ambient temperature.

Alternatively, an alcohol of general formula VII may be prepared from an ester of general formula XXI by firstly removing the protecting group $P^3$ and then reducing the ester group in the compound of general formula XXII so formed to the alcohol. The deprotection of a compound of general formula XXI to give a compound of general formula XXII may be carried out in a manner similar to the deprotection of an alcohol of general formula XV, in cases where $P^3$ is one of the preferred groups by treatment with hydrofluoric acid in aqueous acetonitrile, and the reduction of a compound of general formula XXII to a compound of general formula VII may be carried out in a similar manner to the reduction of an ester of general formula XXI to an alcohol of general formula XV by using a (for example conventional) reducing agent in an inert solvent such as diethyl ether or tetrahydrofuran. It is within the capabilities of one of ordinary skill in the art to select the best alternative of those detailed above, according to the exact nature of the groups $R^{10}$ and $P^3$.

An intermediate of general formula XXI may be prepared from an aldehyde of general formula XX by reaction with an ylid of general formula XXVIII or a compound of the formula $R^9CHHal$ (Hal=halogen, e.g. iodine) in which $R^9$ is $C_{1-6}$ alkyl, $C_{2-6}$ alkenyl, $C_{2-6}$ alkynyl, or $C_{1-3}$ alkyl, $C_{2-3}$ alkenyl, or $C_{2-3}$ alkynyl substituted with substituted phenyl. This is suitable achieved in an inert organic solvent, preferably tetrahydrofuran, at a temperature between $-78°$ C. and ambient. However, a mixture of THF and DMF may be employed instead. It should be appreciated by those skilled in the art that the exact combination of reaction conditions such as solvent, temperature, and reagents used may be varied to produce predominantly one isomer about the newly formed double bond. For example, generation of the ylid by treating ethyl triphenyl-phosphonium bromide with sodium bis(trimethylsilyl)-amide in tetrahydrofuran, at $-78°$ C., then addition of the aldehyde and allowing the mixture to warm to ambient temperature gives a compound in which the newly created alkene is entirely cis $-CH=CHMe$. However, if the ylid is generated using lithium bis(trimethyl-silyl)amide, then a mixture of cis and trans isomers is obtained. This mixture may be carried through the synthetic sequence described above to give a mixture of compounds of general formula I or II, or, preferably, separated using standard techniques and the individual components utilised according to the schemes.

An aldehyde of general formula XX may also be used to introduce acetylenic unsaturation into the group $R^2$ in compounds of the invention. For example, any of the following schemes may be appropriate:

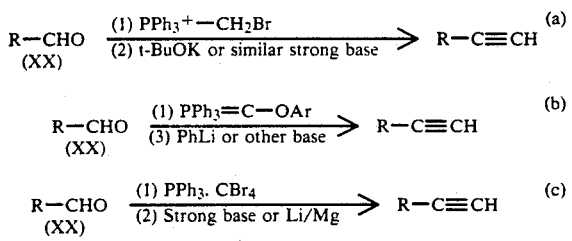

The acetylene $R-C\equiv CH$ can then be deprotonated and substituted with an appropriate electrophilic radical. Scheme (c) is preferred, using lithium amalgam, as a strong base is not required under these conditions.

Acetylenes may also be produced by reacting a compound of general formula XXII ($R-HC=CH-R'$) with $Br_2/CCl_4$ and then with $NaNH_2$ in $NH_3$ or DMSO to form a compound of the general formula $R-HC=CH-R'$, which may subsequently be used as a compound of general formula XXII, although reaction conditions should be selected appropriately to avoid unwanted effects on the ring double bond.

An aldehyde of general formula XX may be prepared from an alcohol of general formula XIX by oxidation, for example using conventional reagents such as pyridinium dichromate or pyridinium chlorochromate, or by using a catalytic quantity of tetra-n-propylammonium per-ruthenate (TRAP) in the presence of N-methylmorpholine N-oxide, in an inert organic solvent, preferably dichloromethane or chloroform at a temperature between 0° C. and ambient; the transformation is most preferably achieved by using Swern's protocol.

Intermediate esters of general formula XXII may also be produced by the reactions outlined in Scheme V, in which $R^5$, $R^9$, and $R^{10}$ are as defined previously, and $R^{12}$ is defined below.

An alcohol of general formula XXV may be reduced to an intermediate of general formula XXII for example by treatment with sodium amalgam in an alcohol such as methanol or ethanol, and preferably buffered using a phosphate salt such as dipotassium (or disodium) hydrogen phosphate.

Alternatively, an alcohol of general formula XXV may be acylated for example with an acid anhydride $((R^{12}CO)_2O)$ or acyl halide ($R^{12}CO.Hal$) and a mild organic base such as pyridine or triethylamine, and preferably using N,N-dimethylaminopyridine as a catalyst, in an inert solvent, preferably dichloromethane or chloroform, to give an intermediate ester of general formula XXVI in which $R^{12}$ may be $C_{1-5}$ alkyl, fluorinated $C_{1-5}$ alkyl, or substituted phenyl, but is preferably methyl, ethyl or phenyl. The acylated compound of general formula XXVI may then be transformed to an alcohol of general formula XXII in the same way that a compound of general formula XXV may be transformed as discussed above, that is for example by treatment with sodium amalgam in a buffered alcoholic solvent.

A keto-sulphone of general formula XXIV may be produced from a lactone of general formula XXIII by reaction with an anion or dianion of a sulphone of general formula XXVII, in an inert organic solvent, preferably tetrahydrofuran, at $-78°$ C. to ambient temperature under an inert atmosphere. Reduction of the ketone group in a compound of general formula XXIV, which may be carried out using conventional reagents such as sodium borohydride, cerium borohydride, lithium triethylborohydride, or lithium aluminium hydride in an inert organic solvent from 0° C. to ambient temperature, and preferably using sodium borohydride in methanol or ethanol at ambient temperature, then gives an alcohol of general formula XXV. The alcohol of general formula XXV thus produced is a mixture of diastereoisomers which may be used as a mixture, or separated and used individually.

It will be apparent to one skilled in the art that the exact combination of reaction conditions and reagents used may be varied to produce predominantly one isomer about the newly formed double bond. For example, in the case in which $R^9$ is methyl, elimination of the alcohol of general formula XXV gave material in which the trans:cis ratio about the new double bond was approximately 6:1. It is within the capabilities of one skilled in the art to select conditions, and to choose between the routes outlined in Schemes IV and V, in order to maximise the production of the desired isomer of esters of general formula XXII. Esters of general formula XXII may then be used to produce compounds of general formulae I or II as detailed in Schemes I to III.

Keto-sulphones of general formula XXIV may also be used to introduce acetylenic unsaturation by reaction first with $(EtO)_2P(O)Cl$ and a mild base and then reduction with sodium amalgam to produce the acetylene analogue of a compound of general formula XXII ($R-HC=CH-R'$). This constitutes a preferred method of synthesis of acetylenes as it avoids the need for a strong base.

Another method of obtaining the intermediate esters of general formula XXI is outlined in Scheme VI in which $R^5$, $R^{10}$, and $P^3$ are as previously defined, and $R^8$ and L are defined below.

An ester of general formula XXI may be obtained by treating an intermediate of general formula XXIX in which L represents a leaving group such as tosyl, mesyl, trifluoromethylsulphonyl, or halide (particularly iodide) with an organometallic reagent that will deliver the group $R^8$ (where $R^8$ is hydrogen, $C_{1-7}$ alkyl, $C_{1-7}$ alkenyl, $C_{1-7}$ alkynyl, or $C_{1-4}$ alkyl, alkenyl, or alkynyl substituted with substituted phenyl) in such a manner that it may be formally represented as a carbanion, in an inert solvent such as diethyl ether or tetrahydrofuran, at a temperature between $-78°$ C. and reflux, under an inert atmosphere.

Examples of suitable organometallic reagents are lithium triethylborohydride, methyl lithium, phenyl lithium, methyl magnesium bromide, lithium acetylide, vinyl lithium, dimethyl copper lithium or other higher order or lower order copper reagents. The exact form of the organometalic reagent used depends on the form of the leaving group present in general formula XXIX, and on the other functionality present in the group $R^8$.

Alternatively, in the case where $R^8$ represents hydrogen, the compound of general formula XXI may be obtained from a compound of general formula XXIX in which L represents iodide by treatment with a hydrogen radical source, for example tributyl tin hydride in an inert solvent such as benzene or toluene.

An intermediate of general formula XXIX may be prepared from an alcohol of general formula XIX for example using conventional, well-known procedures.

Compounds of general formula I in which $R^5$ is methyl may also be obtained from known compounds of general formulae LXX and LXXI (EP-A-0251625), using the methods outlined in reaction Scheme VII in which $R^1$, $R^2$, and L are as previously defined.

Lactones of general formula I may be obtained from the protected lactones of general formula LXXIII preferably by treatment with tetrabutylammonium fluoride in tetrahydrofuran buffered with acetic acid at ambient temperature.

A lactone of general formula LXXIII may be obtained by treating an intermediate of general formula LXXII with an organometallic, preferably organocopper, reagent that will deliver the group $R^8$ (as previously defined) in such a manner that it may be formally represented as a carbanion, for example, dimethyl copper lithium or other higher order or lower order copper reagents, in an inert solvent such as diethyl ether or tetrahydrofuran, at a temperature between $-78°$ C. and ambient, under an inert atmosphere. The exact form of the organometalic reagent used depends on the form of the leaving group present in general formula LXXII, and on the other functionality present in the group $R^8$.

An intermediate of the general formula LXXIII may also be prepared from an aldehyde of the general formula aldehyde LXXI by reaction with an ylid of general formula XXVIII, as defined previously, in an inert organic solvent, preferably tetrahydrofuran, at a temperature between $-78°$ C. and ambient. It should be appreciated by those skilled in the art that the exact combination of reaction conditions such as solvent, temperature, and reagents used may be varied to produce predominantly one isomer about the newly formed double bond in the group $R^2$. Any mixture of double bond isomers may be carried through the synthetic sequence to give compounds of general formula I or II, or (preferably) separated using standard techniques and the individual components utilised according to the schemes.

An intermediate of general formula LXXII may be prepared from an alcohol of general formula LXX for example using conventional, well-known procedures.

Intermediates of general formulae XIX and XXIII in which $R^5$ is methyl, $R^{10}$ is ethyl and $P^3$ is a t-butyldimethylsilyl group, a and b are both single bonds and c is a double bond, are known in the literature. (*J. Chem. Soc., Chem. Commun.*, 1987, 1986). Those intermediates in which $R^5$, $R^{10}$ and $P^3$ are other groups within the appropriate definitions may be prepared using routes analogous to the known route, but using the appropriately different starting materials. Such a change is within the scope of one skilled in the art. Methods for the introduction of a second double bond at a, isomerising to give a single double bond at a or b, or reducing to give a, b and c as single bonds in compounds with structures similar to the compounds of general formulae I, II, IV, V, VII to XII, XIV to XXIX and LXX to LXXIII are known in the art (for examples, see *Tetrahedron* 1986, 42, 4909-4951 or U.S. Pat. No. 4,293,496). Some of these methods may use reagents that under certain conditions deleteriously affect at least some of compounds of general formulae I, II, IV, V, VII to XII, XIV to XXIX and LXX to LXXIII; however, other methods may be suitable for the required transformations in some or all of the compounds of general formulae I, II, IV, V, VII to XII, XIV to XXIX and LXX to LXXIII. Thus it is within the capabilities of one skilled in the art to select appropriate methodology for the interconversion of compounds wherein a, b and c may be single or double bonds (subject to the restrictions mentioned in the description), in order to obtain compounds of general formula I or II with the required single or double bonds at a, b or c.

A phosphonate of general formula XIII in which $R^4$ and $R^{11}$ are methyl and $P^2$ is a t-butyldimethylsilyl group is known in the art (*J. Org. Chem.*, 1988, 53, 2374-2378). Compounds of general formulae XXVII and XXVIII are commercially available or are readily available from commercially available materials using known or analogous methods.

Lactones of general formula XXIII can be used to prepare the corresponding carboxylate compounds of general formula XXXIV, in a decyclisation reaction using a $C_{1-8}$ alkoxy alkali metal compound.

An acylating agent can then be used to provide the R'CO.O. substituent (compounds of general formula XXXIII) present in the final compounds of general formula I and II. Reduction with a reducing agent yields a compound of general formula XXXII. Treatment with an oxidising agent (to a compound of the general formula XXXI) converts the carboxylic acid group to an aldehyde group.

Conversion to a compound of general formula XXX can be achieved by reaction with a compound of the formula $R^9$CHHal (Hal=halogen, e.g. iodine) in the presence of a transition metal (e.g. Cr(II)). Compounds of the general formula X can then be obtained by reaction with a reducing agent.

Compounds of general formula XXXIV can also be used to prepare compounds of general formula XXXV by first protecting the free hydroxy group with a protecting group $P^3$ as previously defined. The intermediates of general formula XIX can then be obtained by treatment with a reducing agent. This is shown in scheme 9, but is not suitable for when $R^6$ represents an alkyl group.

In general, reagents are used in sufficient quantities completely to convert starting materials to products but to be themselves substantially consumed during the course of the reaction. However the amounts may often be varied as is evident to one of ordinary skill in the art. For example, in a reaction of two compounds one of which is not readily available and one of which is, an excess of the readily available compound may be used to drive the reaction further towards completion (unless the use of an excess would increase the synthesis of an undesired compound). Likewise, most of the temperature ranges given in the preceding descriptions are merely exemplary, and it is within the ability of one of ordinary skill in the art to vary those that are not critical.

The reaction times set forth in the preceding description are also merely exemplary and may be varied. As is well-known, the reaction time is often inversely related to the reaction temperature. Generally, each reaction is monitored, for example by thin layer chromatography, and is terminated when at least one starting material is no longer detectably present, or when it appears that no more of the desired product is being formed.

Conventional work-up procedures have generally been omitted from the preceding descriptions.

As utilised in the preceding descriptions, the term "solvent" embraces mixtures of solvents and implies that the reaction medium is a liquid at the desired reaction temperature. It should, therefore, be understood that not all of the solvents listed for a particular reaction may be utilised for the entire cited temperature range. It should also be understood that the solvent must be at least substantially inert to the reactants employed, intermediates generated and end products under the reaction conditions utilised.

The term "inert atmosphere", as utilised in the preceding descriptions, means an atmosphere that does not react with any of the reactants, intermediates or end products or otherwise interfere with the reaction. While a carbon dioxide atmosphere is suitable for certain reactions, the inert atmosphere is usually nitrogen, helium, neon, or argon, or a mixture thereof, and most often dry argon to maintain anhydrous conditions. Most reactions, including those where the use of an inert atmosphere is not specified, are carried out under an inert atmosphere, usually dry argon, for convenience.

The product of each reaction may, if desired, be purified by conventional techniques such as recrystalisation (if a solid), column chromatography, preparative thin layer chromatography, gas chromatography (if sufficiently volatile), fractional distillation under high vacuum (if sufficiently volatile) or high pressure (performance) liquid chromatography (HPLC). Often, however, the crude product of one reaction may be employed in the following reaction without purification or even without isolation.

Some reactions, particularly those utilising strong bases or reducing agents, require anhydrous solvents. Where this is the case solvents may be dried before use using conventional techniques and an inert atmosphere used.

Some of the reactions described above may yield mixtures of two or more products, only one of which leads to the desired compound of general formula I or II. Any mixture so obtained may be separated by conventional techniques such as those set forth in the preceding paragraphs.

Certain of the intermediate compounds described above are believed to be novel, in particular compounds of general formulae IV, XIV and LXXIII. All other intermediate comounds in which either or both of $R^2$ and $R^5$ are not methyl are also believed to be novel.

Compounds of this invention are useful as antihypercholesterolaemic agents for the treatment of arteriosclerosis, hyperlipidaemia, familial hypercholesterolaemia and the like diseases in humans.

According to a third aspect of the invention, there is therefore provided a compound of general formula I or II for use in medicine, particularly as antihypercholesterolaemic agents.

According to a fourth aspect of the invention, there is provided the use of a compound of general formula I or II in the preparation of an antihypercholesterolaemic agent. Compounds of the invention can therefore be used in a method for the treatment or prophylaxis of hypercholesterolaemia in general and arteriosclerosis, familial hypercholesterolaemia or hyperlipidaemia in particular comprising administering to a patient an effective dose of a compound of general formula I or II or a mixture thereof.

According to a fifth aspect of the invention, there is provided a pharmaceutical composition comprising a compound of general formula I or II, or a mixture thereof, and a pharmaceutically acceptable carrier therefor.

A sixth aspect of the present invention relates to a process for the preparation of a pharmaceutical composition of the fifth aspect, the process comprising admixing the carrier and a compound of the general formula I and/or II.

Preferred features of the one aspect of the invention are as for the first *mutatis mutandis*.

Compounds of general formula I and II may be administered orally or rectally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 5 to 100 mg) which may be given in one to four divided doses. Higher doses may be favourably employed as required.

The compounds of this invention may also be co-administered with pharmaceutically acceptable non-toxic cationic polymers capable of binding bile acids in a non-reabsorbable form in the gastrointestinal tract. Examples of such polymers include cholestyramine, colestipol and poly[methyl-(3-trimethylamino-propyl-)iminotrimethylene dihalide]. The relative amounts of the compounds of this invention and these polymers is between 1:100 and 1:15000.

The intrinsic HMG-CoA reductase inhibition activity of the claimed compounds may be measured in in vitro protocols described in detail in the Examples below.

Included within the scope of this invention is the method of treating arteriosclerosis, familial hypercholesterolaemia or hyperlipidaemia which comprises administering to a subject in need of such treatment a nontoxic therapeutically effective amount of the compounds of Formulae I or II or pharmaceutical compositions thereof.

Compounds of general formula IV may also show HMG-CoA reductase inhibition activity and so may be included in the pharmaceutical aspects of the invention.

The following examples show representative compounds encompassed by this invention and their syntheses. However, it should be understood that they are for the purposes of illustration only.

Organic solutions were dried over sodium sulphate or magnesium sulphate, and evaporated under reduced pressure. NMR spectra were recorded at ambient temperature in deuteriochloroform at 250 MHz for proton and 62.5 MHz for carbon unless noted otherwise. All chemical shifts are given in parts per million relative to tetramethylsilane. Infra red spectra were recorded at ambient temperature in solution in chloroform, or in the solid state in a potassium bromide disc as noted.

Chromatography was carried out using Woelm 32-60 m silica.

EXAMPLE 1

Methyl (1S,2S,4aR,6S,8S,8aS,3'R)-7'-(1,2,4a,5,6,7,8,8a-octahydro-2,6-dimethyl-8-[(2'',2''-dimethyl-1''-oxobutyl)oxy]-6-[(E)-prop-1-enyl]-1-naphthalenyl)-3'-hydroxy-5'-oxoheptanoate

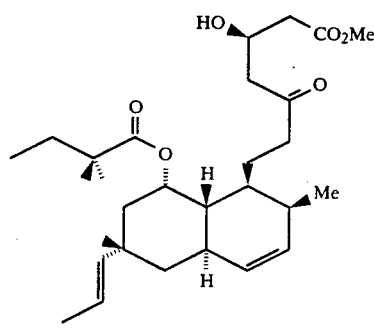

Step 1

Ethyl (1S,2S,4aR,6S,8S,8aS) 8-(tert-Butyldimethylsilyloxy)-6-formyl-2,6-dimethyl-1,2,4a,5,6,7,8,8a-octahydronaphthalene-1-carboxylate (XX)

Acetic acid (11 microL) was added to a suspension of ethyl (1S,2S,4aR,6S,8S,8a) 8-(tert-butyldimethylsilyloxy)-6-hydroxymethyl-2,6-dimethyl-1,2,4a,5,6,7,8,8a-octahydronaphthalene-1-carboxylate (general formula XIX) (39 mg, 0.1 mmol), finely ground pyridinium dichromate (56 mg) and 3 A molecular seives (40 mg) in dry dichloromethane under argon, and the mixture stirred for 100 minutes. Diethyl ether (10 mL) was added, the suspension filtered through celite and silica, then the solvent evaporated to leave the aldehyde (XX) as an oil (37 mg). delta H −0.1 (3H, s), 0.08 (3H, s), 0.84 (3H, d, J 7 Hz), 0.85 (9H, s), 0.94 (3H, s), 1.27 (3H, t, J 7 Hz), 1.4–1.6 (3H, m), 2.14–2.46 (3H, m), 2.58–2.68 (1H, m), 2.67 (1H, dd, J 11 and 6 Hz), 4.0–4.24 (2H, m), 4.38 (1H, m), 5.46 (1H, d, J 10 Hz), 5.54 (1H, ddd, J 10, 4 and 2.5 Hz), 9.47 (1H, d, J 2 Hz)

Step 2

Ethyl (1S, 2S, 4aR, 6S, 8S, 8aS) 1, 2, 4a, 5, 6, 7, 8, 8a-octahydro-2,6-dimethyl-8-(tert-butyldimethylsilyloxy)-6-(E)-prop-1-enylnaphthalene-1-carboxylate (XXI)

THF (90 mL) was added to chromium (II) chloride (5.3 g, 43 mmol) under an argon atmosphere. After stirring the mixture until a fine suspension resulted a solution of the aldehyde (XX) (2.2 g, 5.38 mmole) and 1,1-diiodoethane (3.05 g, 10.8 mmole) in THF (30 mL) was added. The reaction mixture was then stirred for 16 hours, water (200 mL) was added and stirring continued for 5 minutes. The THF was removed under vaccuum and the aqueous mixture extracted with ether (3×100 mL). The combined ethereal layers were washed with brine (100 mL), dried and evaporated to leave a green oil. This was purified by chromatography eluting with ether, to give the olefin (XXI) as a colourless oil (2.21 g).

TLC: Rf 0.34 (hexane:ethyl acetate, 19:1)

Step 3

(1S, 2S, 4aR, 6S, 8S, 8aS)-1, 2, 4a, 5, 6, 7, 8, 8a-octahydro-8-(tert-butyldimethylsilyloxy)-1-hydroxymethyl-2,6-dimethyl-6-((E)-prop-1-enyl)naphthalene (XV)

A solution of the ester from the previous step (2.21 g, 5.38 mmole) in dry THF (25 mL) was added dropwise to a stirred solution of lithium aluminium hydride in dry THF (1M, 10.7 mmole) under argon. After twenty hours, the suspension was cooled in an ice bath and water (1 mL) was added dropwise, followed by sodium hydroxide solution (15%, 1 mL) and water (3 mL). The mixture was filtered, the solid washed with diethyl ether and the organics evaporated under reduced pressure to leave the crude alcohol (1.90 g) as an oil which was used without purification in the next step.

Step 4

(1S,3S,4aR,6S,8S,8aS)-1-Hydroxy-8-hydroxymethyl-3,7-dimethyl-1,2,3,4,4a,7,8,8a-octahydro-3-((E)-prop-1-enyl)naphthalene (VII)

The alcohol from the previous step (1.90 g) was stirred at room temperature under argon in 19:1 acetonitrile: aqueous hydrofluoric acid (40%) (50 ml) for 46 hours. Saturated aqueous sodium bicarbonate solution (200 ml) was added, and the mixture extracted with ethyl acetate (3×200 mL). The organic solution was dried (MgSO4) and the solvent removed to give a gum which was purified by chromatography on silica eluting with ethyl acetate:hexane (3:7) to give the diol (VII) (1.09 g).

Step 5

(1S, 2S, 4aR, 6S, 8S, 8aS)-1-(tert-butyldimethylsilyl)oxymethyl-1, 2, 4a, 5, 6, 7, 8, 8a-octahydro-8-hydroxy-2,6-dimethyl-6-((E)-prop-1-enyl) naphthalene (VIII)

t-Butyldimethylsilyl chloride (0.74 g, 4.92 mmole) was added in portions to a stirred solution of the diol from the previous step (1.07 g, 4.28 mmole) and imidazole (0.386 g, 5.4 mmole) in dry dichloromethane (20 mL). The mixture was stirred for 18 hours then partitioned between dichloromethane (200 mL) and 0.5M hydrochloric acid (25 mL). The organic phase was separated and washed successively with water (100 mL), saturated sodium bicarbonate solution (100 mL) and brine (50 mL) then dried and evaporated to give the crude monosilyl ether as a gum (1.53).

Step 6

(1S, 2S, 4aR, 6S, 8S, 8aS, 2'S)-1, 2, 4a, 5, 6, 7, 8, 8a-octahydro-2,6-dimethyl-8-[(2',2'-dimethyl-1'-oxobutyl)oxy]-6-[(E)-prop-1-enyl]naphthalene-1-carbaldehyde (XII)

2,2-Dimethylbutyryl chloride (3.39 g, 5.37 mmole) and 4-dimethylaminopyridine (DMAP; 90 mg) were added to a solution of alcohol from the previous step (1.53 g, 4.2 mmole) in dry pyridine (50 mL) and the solution heated to 100° C. for 16 hours under argon. The mixture was cooled and the solvent evaporated. The residue was partitioned between diethyl ether (150 mL) and 0.5M hydrochloric acid (75 mL). The organic phase was separated and washed with water (50 mL) and saturated sodium bicarbonate solution (50 mL), then dried and evaporated to give the acylated product (IX) as a gum which was purified by chromatography on silica, eluting with ethyl acetate:hexane (1.49).

A solution of the silylated ester (IX) prepared above (296 mg, 0.64 mmole) in 40% aqueous HF:acetonitrile (1:19) (6.4 mL) was stirred for 80 minutes then saturated sodium bicarbonate solution (20 mL) and ethyl acetate (50 mL) added, the aqueous phase separated and further extracted with ethyl acetate (50 mL). The combined organic layers were dried and evaporated to leave the alcohol (X) as a gum, (213 mg), which was used directly in the next stage.

Acetic acid (70 microL) was added to a suspension of the alcohol (X) prepared in the previous stage (213 mg, 0.6 mmol), finely ground pyridinium dichromate (345 mg) and 3 A molecular sieves (213 mg) in dry dichloromethane (6 mL) under argon, and the mixture stirred for 30 minutes. Diethyl ether (50 mL) was added, the suspension filtered through celite and silica, then the solvent evaporated to leave the aldehyde (XII) as an oil (204 mg).

Step 7

Methyl (1S, 2S, 4aR, 6S, 8S, 8aS, 3'R)-7'-(1, 2, 4a, 5, 6, 7, 8, 8a-octahydro-2,6-dimethyl-8-[(2",2"-dimethyl-1"-oxobutyl)oxy]-6[(E)-prop-1-enyl-1-]naphthalenyl)-3'-t-butyldimethylsilyloxy-5'-oxohept-6'-enoate (XIV)

A solution of lithium hexamethyldisilazide in tetrahydrofuran (1.0M, 0.62 mmole) was added dropwise to a cold (−70° C.) stirred solution of methyl 3(R)-(t-butyldimethylsilyloxy)-5-oxo-6-(dimethylphosphonyl) hexanoate (general formula XIII; 263 mg, 0.68 mmole) in THF (0.3 mL) under argon. After 15 minutes, a solution of aldehyde (XII) (95 mg, 0.3 mmole) in THF (0.3 mL) was added, the solution allowed to warm to room temperature and stirred for 64 hours. The reaction was quenched with saturated ammonium chloride solution (5 mL) and extracted with dichloromethane (3×10 mL), which was dried and evaporated to leave a gum. Purification by column chromatography eluting with ethyl acetate:hexane (1:20), gave the enone (XIV) (45 mg).

Step 8

Methyl (1S,2S,4aR,6S,8S,8aS,3'R)-7'-(1,2,4a,5,6,7,8,8a-octahydro-2,6-dimethyl-8-[(2",2"-dimethyl-1"-oxobutyl)oxy]-6-[(E)-prop-1-enyl]-1-naphthalenyl)-3'-hydroxy-5'-oxoheptanoate A solution of methyl (1S, 2S, 4aR, 6S, 8S, 8aS, 3'R)-7'-(1, 2, 4a, 5, 6, 7, 8, 8a-octahydro-2,6-dimethyl-8-[(2",2"-dimethyl-1"-oxobutyl)oxy]-6-[(E)-prop-1-enyl]-1-naphthalenyl)-3'-t-butyldimethylsilyloxy-5'-oxohept-6'-enoate (general formula XIV) (57 mg, 0.099 mmol) and ammonium chloride (280 mg, 5.2 mmol) in deoxygenated ethanol was stirred at room temperature under argon, and sodium hydrogen telluride solution (0.26M in ethanol, 2.0 mL, 0.52 mmol) was added. A further quantityies of the telluride was added after 3 hours (2.0 mL). After stirring for a further 20 minutes the solvent was evaporated and the residue partitioned between dichloromethane (4×25 mL) and saturated ammonium chloride solution (20 mL). The organic layer was dried and the solvent evaporated to leave a clear oil (52 mg).

The oil was taken up in 1 mL of 19:1 acetonitrile:aqueous hydrofluoric acid (40%), the mixture stirred for 70 minutes at room temperature, then diluted with ethyl acetate (25 mL). After washing with saturated aqueous sodium bicarbonate solution (10 mL) and brine (10 mL), the organic solution was dried and evaporated to leave a yellow oil, which was purified by chromatography eluting with hexane:ethyl acetate (7:3) to leave the alcohol as a white solid (41 mg, 84%).

delta H 0.79–0.86 (6H, m), 0.94 (3H, s), 0.98–1.75 (8H, m), 1.12 (3H, s), 1.13 (3H, s), 1.62 (3H, dd, J=6.3 and 1.4 Hz), 1.83 (1H, br d, J=13 Hz), 2.02 (1H, d, J 15 Hz), 2.1–2.3 (2H, m), 2.4–2.5 (2H, m), 2.50 (2H, d, J 6 Hz), 2.6 (2H, d, J 5.3 Hz), 3.38 (1H, br m), 3.70 (3H, s), 4.43 (1H, m), 5.13 (1H, m), 5.25–5.38 (1H, obscured double quartet, J 15.7 and 6.3 Hz), 5.4 (1H, br d, J 10.3 Hz), 5.53 (1H, br d, J 15.8 Hz), 5.62 (1H, ddd, J 9.6, 4.8, and 2.5 Hz)

EXAMPLE 2

Methyl (1S,2S,4aR,6S,8S,8aS,3'R,5'R)-7'-(1,2,4a,5,6,7,8,8a-octahydro-2,6-dimethyl-8-[(2",2"-dimethyl-1"-oxobutyl)oxy]-6-[(E)-prop-1-enyl]-1-naphthalenyl)-3',5'-dihydroxyheptanoate

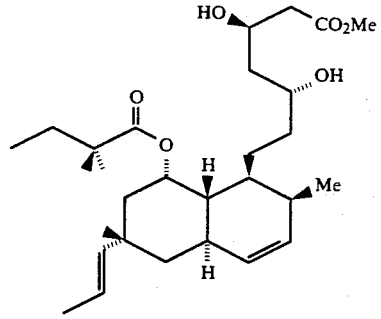

A solution of triethylborane (1.0M in THF; 0.096 mmole) was added to a stirred solution of MeOH (0.19 mL) in THF (0.77 mL) under argon. After 1 hour, the mixture was cooled to −70° C., and a solution of the ketone of example 1 (38 mg, 0.084 mmole) in THF:MeOH (4:1, 0.96 mL) was added dropwise and stirred a further 1 hour. Sodium borohydride (3.5 mg, 0.092 mmole) was added rapidly under argon, the solution stirred for 2.5 hours, then warmed to room temperature and quenched with saturated ammonium chloride solution (1 mL). The mixture was stirred for 15 minutes, acidified with 2M hydrochloric acid (1 mL) and extracted with ethyl acetate (3×10 mL). The combined ethyl acetate extracts were washed with sodium bicarbonate solution, dried and evaporated to give the diol as a gum (35 mg, 92%).

delta H 0.8–0.9 (6H, m), 0.94 (3H, s), 1.0–2.0 (24H, m), 2.3 (1H, m), 2.5 (1H, m), 2.50 (2H, d, J 6 Hz), 3.73 (3H, s), 3.8 (1H, m), 4.25 (1H, m), 5.15 (1H, m), 5.25–5.38 (1H, obscured double quartet, J 15.7 and 6.3 Hz), 5.4 (1H, br d, J 10.3 Hz), 5.53 (1H, br d, J 15.8 Hz), 5.62 (1H, ddd, J 9.6, 4.8, and 2.5 Hz)

EXAMPLE 3

(1S,2S,4aR,6S,8S,8aS,4'R,6'R)-6'-{2-(1,2,4a,5,6,7,8,8a--octahydro-2,6-dimethyl-8-[(2'',2''-dimethyl-1''-oxobutyl)oxy]-6-[(E)-prop-1-enyl]-1-naphthalenyl)ethyl}-tetrahydro-4'-hydroxy-2H-pyran-2'-one

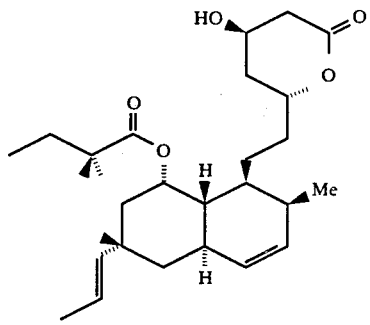

A solution of the diol of example 2 (35 mg, 0.071 mmole) in 19:1 acetonitrile:aqueous hydrofluoric acid (40%) (1.42 mL) was stirred for 4 hours then neutralised with sodium bicarbonate solution. The mixture was extracted with ethyl acetate (3×20 mL), dried and evaporated to leave a gum (28 mg), which was purified by column chromatography eluting with ethyl acetate:-hexane (1:1) to give the lactone as a gum (23 mg, 70%).

delta H 0.82-0.88 (6H, m), 0.95 (3H, s), 0.99-2.01 (14H, m), 1.3 (3H, s), 1.14 (3H, s), 1.64 (3H, dd, J 6 and 1 Hz), 2.33 (1H, m), 2.48 (2H, m), 2.61 (1H, br dd, J 17, and 3.6 Hz), 2.73 (1H, dd J 17 and 5 Hz), 4.36 (1H, m), 4.60 (1H, m), 5.15 (1H, m), 5.25-5.34 (1H, dq, J 16 and 6 Hz), 5.4 (1H, br d, J 10.3 Hz), 5.53 (1H, br d, J 15.8 Hz), 5.62 (1H, ddd, J 9.6, 4.8 and 2.5 Hz)

delta C 176.3, 169.0, 138.5, 131.0, 129.3, 118.2, 74.9, 68.5, 61.2, 42.5, 42.2, 41.6, 40.4, 37.1, 35.8, 34.6, 34.0, 31.5, 31.4, 31.2, 30.5, 29.9, 23.2, 21.9, 16.9, 13.5, 7.8

EXAMPLE 4

Sodium (1S,2S,4aR,6S,8S,8aS,3'R,5'R)-7'-(1,2,4a,5,6,7,8,8a-octahydro-2,6-dimethyl-8-[(2'',2''-dimethyl-1''-oxobutyl)oxy]-6-[(E)-prop-1-enyl]-1-naphthalenyl)-3',5'-dihydroxyheptanoate

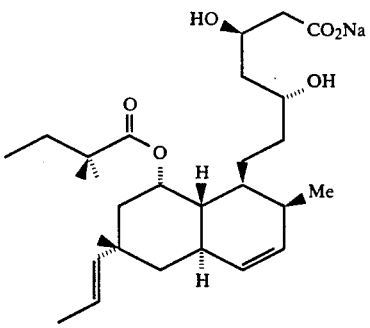

The lactone of example 3 (3.7 mg, 8.0 micromole) was dissolved in 0.068M sodium hydroxide solution in 2:1 methanol:water (125 microL, 8.5 micromole) and left at room temperature for 18 hours. Evaporation of the solvent left the salt as a gum.

What is claimed is:

1. A compound selected from the group consisting of general formulae I and II:

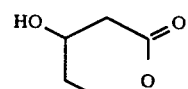
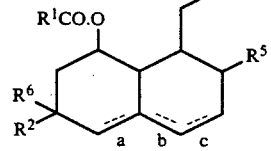

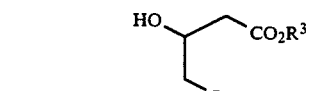
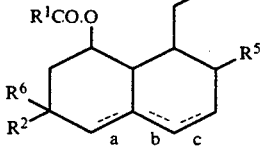

wherein:
$R^1$ represents a $C_{1-8}$ alkyl, $C_{3-8}$ cycloalkyl, $C_{3-8}$ cycloalkyl($C_{1-8}$)alkyl, $C_{2-8}$ alkenyl, or $C_{1-6}$ alkyl substituted phenyl group;

$R^2$ represents $C_{2-5}$ alkenyl or $C_{2-5}$ alkenyl substituted with substituted phenyl group;

$R^3$ represents a hydrogen atom or $R^4$ or M;

$R^4$ represents a $C_{1-5}$ alkyl group, or a $C_{1-5}$ alkyl group substituted with a group chosen from substituted phenyl, dimethylamino and acetylamino;

$R^5$ represents a hydrogen atom or a methyl or ethyl group;

$R^6$ represents a $C_{1-8}$ alkyl, $C_{2-8}$ alkenyl or a $C_{2-8}$ alkynyl group or a $C_{1-5}$ alkyl, $C_{2-5}$ alkenyl or a $C_{2-5}$ alkynyl group substituted with a substituted phenyl group;

wherein the term "substituted", as applied to the phenyl group, means substituted with up to four substituents each of which independently may be $C_{1-6}$ alkyl, $C_{1-6}$ alkoxy, hydroxy, thiol, amino, halo (including fluoro, chloro, bromo, and iodo), trifluoromethyl or nitro;

M represents a cation capable of forming a pharmaceutically acceptable salt;

Q represents C=O or CHOH; and each of a, b, c, and d is independently a single or double bond except that when a and c are double bonds then b is a single bond.

2. A compound according to claim 1 wherein:
$R^1$ represents $C_{4-6}$ branched alkyl;
$R^3$ and $R^4$ represent $C_{1-5}$ alkyl;
$R^6$ represents $C_{1-5}$ alkyl;
Q represents CHOH; and
b and d are both single bonds, and one or both of a and c are double bonds.

3. A compound according to claim 1, wherein $R^1$ represents a $C_{4-6}$ branched alkyl group; $R^2$ represents a $C_{2-6}$ alkenyl group; each of a and c independently represents a single or double bond; and each of b and d represents a single bond.

4. A compound according to claim 1, wherein $R^1$ represents a $C_{4-5}$ branched alkyl group; $R^2$ represents (E)-prop-1-enyl; and $R^5$ represents methyl.

5. A compound according to claim 1, wherein $R^1$ represents a branched $C_4$ alkyl group; $R^2$ represents prop-1-enyl; $R^3$ represents methyl or ethyl; $R^5$ represents methyl; $R^6$ represents methyl; and Q represents the group CHOH.

6. A compound selected from the group consisting of:
(A) (1S,2S,4aR,6S,8S,8aS,4'R,6'R)-6'-{2-(1,2,4a,5,6,7,8,8a-octahydro-2,6-dimethyl-8-[(2'',2''-dimethyl-1''-oxobutyl)oxy]-6-[(E)-prop-1-enyl]-1-naphthalenyl)ethyl}-tetra-hydro-4'-hydroxy-2H-pyran-2'-one,
(B) Sodium (1S,2S,4aR,6S,8S,8aS,3'R,5'R)-7'-(1,2,4a,5,6,7,8,8a-octahydro-2,6-dimethyl-8-[(2'',2''''-dimethyl-1''-oxobutyl)oxy]-6-[(E)-prop-1-enyl]-1-naphthalenyl)-3',5'-dihydroxyheptanoate,
(C) Methyl (1S,2S,4aR,6S,8S,8aS,3'R,5'R)-7'-(1,2,4a,5,6,7,8,8a-octahydro-2,6-dimethyl-8-[(2'',2''-dimethyl-1''-oxobutyl)oxy]-6-[(E)-prop-1-enyl]-1-naphthalenyl)-3',5'-dihydroxyheptanoate, and
(D) Methyl (1S,2S,4aR,6S,8S,8aS,3'R)-7'-(1,2,4a,5,6,7,8,8a-octahydro-2,6-dimethyl-8-[(2'',2''-dimethyl-1''-oxobutyl)oxy]-6-[(E)-prop-1-enyl]-1-naphthalenyl)-3'-hydroxy-5'-oxoheptanoate.

* * * * *